United States Patent [19]

Katsuda et al.

[11] Patent Number: 4,459,305

[45] Date of Patent: Jul. 10, 1984

[54] CYCLOPROPANECARBOXYLIC ACID ESTER DERIVATIVES, A METHOD OF MANUFACTURING THEM, AND THEIR USES

[75] Inventors: Yoshio Katsuda, Nishinomiya; Yoshihiro Minamite, Osaka, both of Japan

[73] Assignee: Dainippon Sochugiku Kabushiki Kaisha, Osaka, Japan

[21] Appl. No.: 329,273

[22] PCT Filed: Apr. 10, 1981

[86] PCT No.: PCT/JP81/00084

§ 371 Date: Dec. 4, 1981

§ 102(e) Date: Dec. 4, 1981

[87] PCT Pub. No.: WO81/02892

PCT Pub. Date: Oct. 15, 1981

[30] Foreign Application Priority Data

Apr. 10, 1980 [JP] Japan .................. 55-047233
Apr. 26, 1980 [JP] Japan .................. 55-55960

[51] Int. Cl.³ .............. A01N 53/00; C07C 69/74; C07C 121/75; C07D 209/48
[52] U.S. Cl. .............. 424/274; 260/465 D; 548/479; 548/530; 549/58; 549/79; 549/469; 549/488; 424/275; 424/285; 424/304; 424/305; 560/124
[58] Field of Search .............. 260/465 D; 548/479, 548/530; 549/58, 79, 469, 488; 424/275, 274, 285, 304, 305; 560/124

[56] References Cited

U.S. PATENT DOCUMENTS 4,279,835 6/1981 Martel et al. .................. 260/465 D
4,299,839 11/1981 Omura et al. .................. 424/274

*Primary Examiner*—Dolph H. Torrence
*Attorney, Agent, or Firm*—Parkhurst & Oliff

[57] ABSTRACT

The present invention relates to a cyclopropanecarboxylic acid ester derivative of the general formula I:

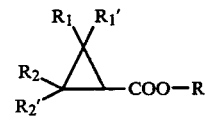

in which $R_1$ stands for a hydrogen atom, a methyl group, a halogen atom or a halomethyl group, $R_1'$ stands for a halomethyl or haloethyl group, $R_2$ and $R_2'$ are the same or different, each standing for methyl group, a halogen atom or a halomethyl group, provided that if $R_1$ is a hydrogen atom, $R_1'$ is a halomethyl group, and $R_2$ and $R_2'$ are each a methyl group, and R stands for a group of the formula II, III, IV, V or VI:

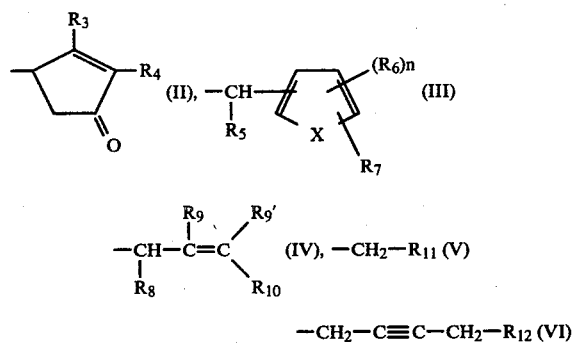

in which $R_3$ stands for a hydrogen atom or a methyl group, $R_4$ stands for an allyl, propargyl, benzyl or 2,4-pentadienyl group, X stands for an oxygen or sulfur atom, or a —CH=CH— group, $R_5$ stands for a hydrogen atom, or a cyano, ethynyl, propynyl or trifluoromethyl group, $R_6$ stands for a hydrogen or halogen atom or a methyl or trifluoromethyl group, n is an integer of 1 to 4, $R_7$ stands for a halogen atom, a lower alkyl, lower haloalkoxy or lower haloalkoxymethyl group, an allyl, propargyl, benzyl, benzoyl or phenoxy group, a phenoxy group having one hydrogen atom in the benzene ring replaced by a halogen atom, or a methyl or lower alkoxy group, or a dichlorovinyloxy group, $R_5$ and $R_6$ may have their ends bonded to each other to form an ethylene or methyleneoxy chain, and $R_6$ and $R_7$ may have their ends bonded to each other to form a trimethylene or tetramethylene chain, $R_8$ stands for a hydrogen atom or an ethynyl group, $R_9$ and $R_9'$ each stand for a hydrogen or halogen atom, or a methyl group, $R_{10}$ stands for a phenyl or benzyl group, or an alkyl, alkenyl or alkynyl group having 2 to 4 carbon atoms, $R_{11}$ stands for a tetrahydrophthalimide or dialkylmaleimide group, and $R_{12}$ stands for a phenyl or phenoxy group; and an optical or geometrical isomer thereof, a process for manufacturing the same and an insecticide and an acaricide containing the same as an active ingredient. In particular, the compounds according to the present invention are stable against light and exhibit excellent insecticidal and arcaricidal actions.

14 Claims, No Drawings

CYCLOPROPANECARBOXYLIC ACID ESTER DERIVATIVES, A METHOD OF MANUFACTURING THEM, AND THEIR USES

TECHNICAL FIELD

This invention relates to novel cyclopropanecarboxylic acid ester derivatives having the action of killing insects and ticks, a method of manufacturing those derivatives, and an insecticide and acaricide containing such a derivative as its active ingredient.

BACKGROUND ART

In esters of chrysanthemumic acid which are known as insecticides, various kinds of alcohol components have been studied, and the esters employing such alcohols have been put to practical use. These crysanthemumic esters are, however, liable to be decomposed through oxidation upon exposure to light, and their outdoor use is, therefore, limited. Much recent research has been directed to the acid components of those esters. As a result, there are known compounds which are more stable against light than pyrethroid, for example, esters of dihalovinylcrysanthemumic acid of the formula (X) with halogen atoms substituted for methyl groups:

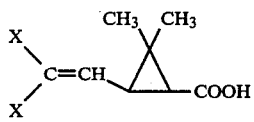

in which X stands for a halogen atom, and esters of tetramethylcyclopropanecarboxylic acid of the formula XI:

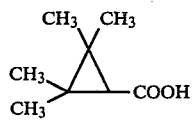

The esters of the acid represented by the formula XI have difficulties unsolved in practical use, since it is inferior in insecticidal activity to the esters of chrysanthemumic acid or those of the acids of the formula X, and higher in toxicity to men and cattle. The esters of the acids of the formula X are not always acceptable, either, in view of the problems of environmental pollution, chromic toxicity, etc.

As a result of strenuous researches, the inventors of this invention have discovered that if some of its methyl groups are replaced by halogen atoms or halomethyl groups, the esters of the acid represented by the formula XI surprisingly have remarkably improved insecticidal activities and largely reduced toxicities. The esters of the novel cyclopropanecarboxylic acids compared with the esters of the non-replaced acid exhibit far higher stabilities against light than the known chrysanthemumic acid esters.

The present invention has been accomplished on the basis of the above-mentioned knowledge.

DISCLOSURE OF THE INVENTION

This invention relates to novel cyclopropanecarboxylic acid ester derivatives of the general formula I:

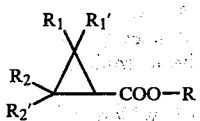

in which $R_1$ stands for a hydrogen atom, a methyl group, a halogen atom, or a halomethyl group, $R_1'$ stands for a halomethyl or haloethyl group, $R_2$ and $R_2'$ are the same or different, each standing for any one of a methyl group, a halogen atom, and a halomethyl group, provided that if $R_1$ is a hydrogen atom, $R_1'$ is a halomethyl group, and $R_2$ and $R_2'$ are each a methyl group, and R stands for a group of the formula II, III, IV, V or VI:

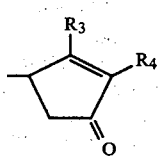

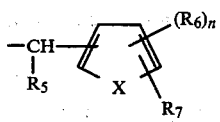

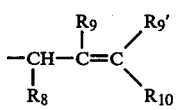

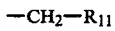

in which $R_3$ stands for a hydrogen atom or a methyl group, $R_4$ stands for an allyl, propargyl, benzyl or 2,4-pentadienyl group, X stands for an oxygen or sulfur atom, or a —CH=CH— group, $R_5$ stands for a hydrogen atom or a cyano, ethynyl, propynyl or trifluoromethyl group, $R_6$ stands for a hydrogen atom, a methyl group, a halogen atom or a trifluoromethyl group, n is an integer of 1 to 4, $R_7$ stands for a halogen atom, a lower alkyl, lower haloalkoxy or lower haloalkoxymethyl group, an allyl, propargyl, benzyl, benzoyl or phenoxy group, a phenoxy group having one hydrogen atom in the benzene ring replaced by a halogen atom, a methyl or lower alkoxy group, or a dichlorovinyloxy group, $R_5$ and $R_6$ may have their ends bonded to each other to form an ethylene or methyleneoxy chain, and $R_6$ and $R_7$ may have their ends bonded to each other to form a trimethylene or tetramethylene chain, $R_8$ stands for a hydrogen atom or an ethynyl group, $R_9$ and $R_9'$ stand for a hydrogen atom, a methyl group or a halogen atom, $R_{10}$ stands for a phenyl or benzyl group, or an alkyl, alkenyl or alkynyl group having 2 to 4 carbon atoms, $R_{11}$ stands for a tetrahydrophthalimide or dialkylmaleimide group, and $R_{12}$ stands for a phenyl or phenoxy group, and the optical or geometrical isomer thereof. The invention also relates to a method of manufacturing such compounds, and insecticides and acaricides containing such compounds as an effective ingredient.

The compounds of the formula I are excellent insecticidal compositions which overcome the drawback of the conventionally known chrysanthemumic ester pyrethroid of lacking stability against light, and which have both wide insecticidal spectrums and low degrees of toxicity. Moreover, the cyclopropanecarboxylic acids constituting the compounds of the formula I are easily obtainable with low costs.

The compound of the formula I, which may be used as an active ingredient in this invention, can be prepared, according to the ordinary process for producing esters, by reacting a carboxylic acid of the general formula VIII:

(VIII)

in which $R_1$ stands for a hydrogen or halogen atom, or a methyl or halomethyl group, $R_1'$ stands for a halomethyl or haloethyl group, and $R_2$ and $R_2'$ are the same or different, each standing for a halogen atom, or a methyl or halomethyl group, provided that if $R_1$ is a hydrogen atom, $R_1'$ is a halomethyl group, and $R_2$ and $R_2'$ stand for a methyl group, or a reactive derivative thereof, with an alcohol of the general formula IX:

HO-R     (IX)

in which R stands for a group of the formula II, III, IV, V or VI:

(II)

(III)

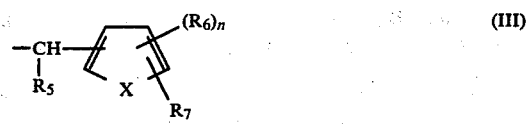
(IV)

—CH$_2$—R$_{11}$   (V)

—CH$_2$—C≡C—CH$_2$—R$_{12}$   (VI)

in which $R_3$ stands for a hydrogen atom or a methyl group, $R_4$ stands for an allyl, propargyl, benzyl or 2,4-pentadienyl group, X stands for an oxygen or sulfur atom, or a —CH=CH— group, $R_5$ stands for a hydrogen atom or a cyano, ethynyl, propynyl or trifluoromethyl group, $R_6$ stands for a hydrogen or halogen atom, or a methyl or trifluoromethyl group, n is an integer of 1 to 4, $R_7$ stands for a halogen atom, a lower alkyl, lower haloalkoxy or lower haloalkoxymethyl group, an allyl, propargyl, benzyl, benzoyl or phenoxy group, a phenoxy group in which one hydrogen atom in the benzene ring has been replaced by a halogen atom, or a methyl or lower alkoxy group, or a dichlorovinyloxy group, $R_5$ and $R_6$ may have their ends bonded to each other to form an ethylene or methyleneoxy chain, and $R_6$ and $R_7$ may have their ends bonded to each other to form a trimethylene or tetramethylene chain, $R_8$ stands for a hydrogen atom or an ethynyl group, $R_9$ and $R_9'$ each stand for a hydrogen or halogen atom or a methyl group, $R_{10}$ stands for a phenyl or benzyl group, or an alkyl, alkenyl or alkynyl group having 2 to 4 carbon atoms, $R_{11}$ stands for a tetrahydrophthalimide or dialkylmaleimide group, and $R_{12}$ stands for a phenyl or phenoxy group, or a reactive derivative thereof. Examples of the reactive derivative of a carboxylic acid include an acid halide, an acid anhydride, a lower alkyl ester, and an alkali metal salt. Examples of the reactive derivative of an alcohol include chloride, bromide and p-toluenesulfonate. The reaction may be carried out in an appropriate solvent, if necessary, in the presence of a deacidifying agent, or an organic or inorganic base or acid as a catalyst, and if necessary, under heat. If different combinations of the substituents $R_1$ and $R_1'$, and $R_2$ and $R_2'$ are employed for the acid components of the compounds represented by the formula I, at least one asymmetric carbon atom occurs, and an ordinary synthesis process provides a racemic mixture. All of those compounds belong to the scope of this invention. The same is true of the cases in which the alcohol contains asymmetric carbon. The following is a list of typical examples of the compounds represented by the formula I, though they, of course, do not limit the scope of this invention:

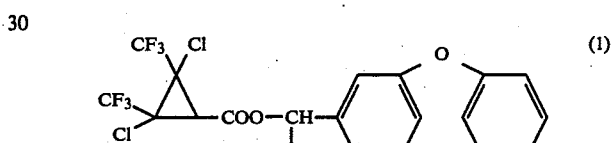
(1)

3'-Phenoxy-α'-cyanobenzyl 2,3-dichloro-2,3-ditrifluoromethylcyclopropanecarboxylate, $n_D^{20}$ 1.5513

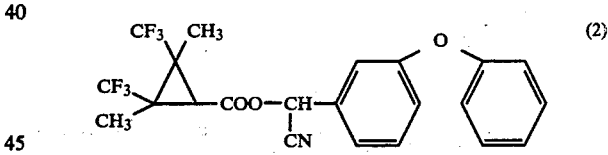
(2)

3'-Phenoxy-α'-cyanobenzyl 2,3-dimethyl-2,3-ditrifluoromethylcyclopropanecarboxylate, $n_D^{20}$ 1.5425

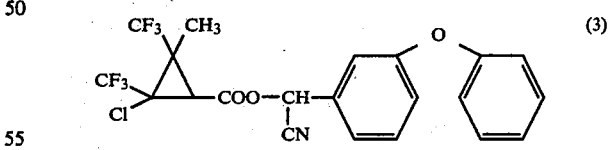
(3)

3'-Phenoxy-α'-cyanobenzyl 2-methyl-3-chloro-2,3-ditrifluoromethylcyclopropanecarboxylate, $n_D^{20}$ 1.5480

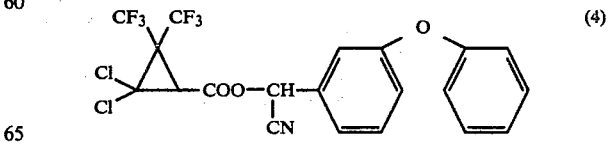
(4)

3'-Phenoxy-α'-cyanobenzyl 2,2-ditrifluoromethyl-3,3-dichlorocyclopropanecarboxylate, $n_D^{20}$ 1.5508

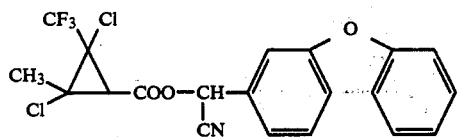

3'-Phenoxy-α'-cyanobenzyl 2-trifluoromethyl-3-methyl-2,3-dichlorocyclopropanecarboxylate, $n_D^{20}$ 1.5526

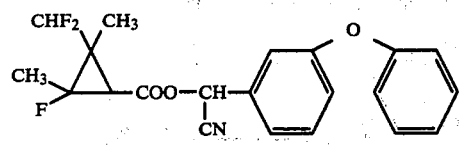

3'-Phenoxy-α'-cyanobenzyl 2-difluoromethyl-3-fluoro-2,3-dimethylcyclopropanecarboxylate, $n_D^{20}$ 1.5417

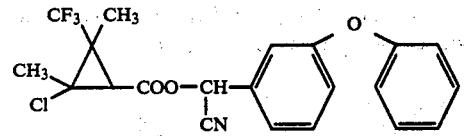

3'-Phenoxy-α'-cyanobenzyl 2-trifluoromethyl-3-chloro-2,3-dimethylcyclopropanecarboxylate, $n_D^{20}$ 1.5492

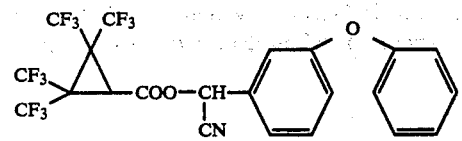

3'-Phenoxy-α'-cyanobenzyl 2,2,3,3-tetratrifluoromethylcyclopropanecarboxylate, $n_D^{20}$ 1.5415

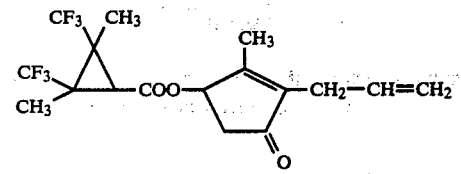

2'-Allyl-3'-methyl-2'-cyclopentene-1'-one-4'-yl 2,3-dimethyl-2,3-ditrifluoromethylcyclopropanecarboxylate, $n_D^{20}$ 1.5173

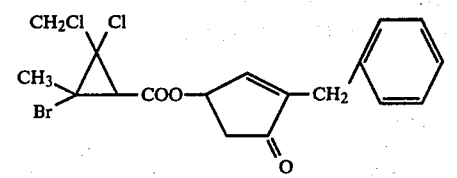

2'-Benzyl-2'-cyclopentene-1'-one-4'-yl 2-chloro-2-chloromethyl-3-methyl-3-bromocyclopropanecarboxylate, $n_D^{20}$ 1.5530

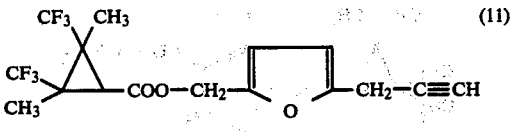

5'-Propargyl-2'-furylmethyl 2,3-dimethyl-2,3-ditrifluoromethylcyclopropanecarboxylate, $n_D^{20}$ 1.5914

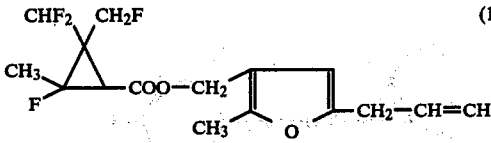

5'-Allyl-2'-methyl-3'-furylmethyl 2-fluoromethyl-2-difluoromethyl-3-methyl-3-fluorocyclopropanecarboxylate, $n_D^{20}$ 1.5230

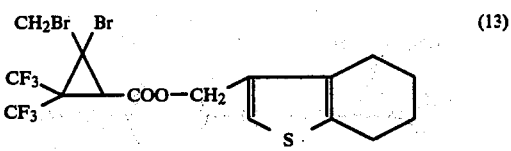

4,5'-Tetramethylene-3'-thenyl 2-bromomethyl-2-bromo-3,3-ditrifluoromethylcyclopropanecarboxylate, $n_D^{20}$ 1.5418

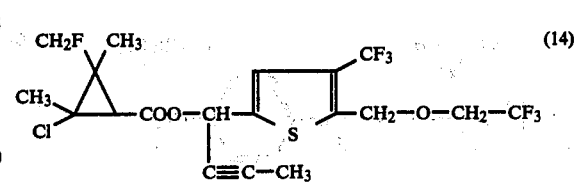

4'-Trifluoromethyl-5'-(2,2,2-trifluoroethoxymethyl)-α'-propynyl-2'-thenyl 2-fluoromethyl-3-chloro-2,3-dimethylcyclopropanecarboxylate, $n_D^{20}$ 1.5527

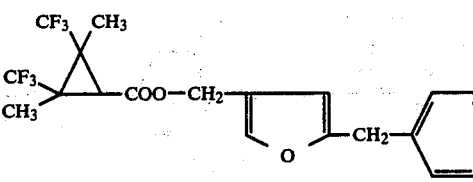

5'-Benzyl-3'-furylmethyl 2,3-dimethyl-2,3-ditrifluoromethylcyclopropanecarboxylate, $n_D^{20}$ 1.5486

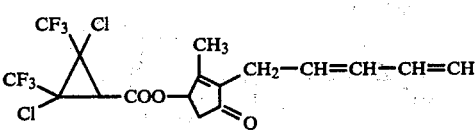

2'-(2,4-Pentadienyl)-3'-methyl-2'-cyclopentene-1'-one-4'yl 2,3-dichloro-2,3-ditrifluoromethylcyclopropanecarboxylate, $n_D^{20}$ 1.5391

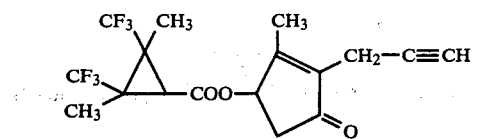 (17)

2'-Propargyl-3'-methyl-2'-cyclopentene-1'-one-4'-yl 2,3-dimethyl-2,3-ditrifluoromethylcyclopropanecarboxylate, $n_D^{20}$ 1.5253

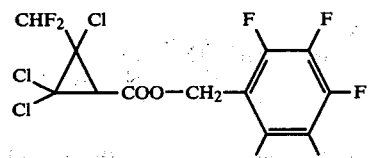 (18)

2',3',4',5',6'-Pentafluorobenzyl 2-difluoromethyl-2,3,3-trichlorocyclopropanecarboxylate, $n_D^{20}$ 1.5329

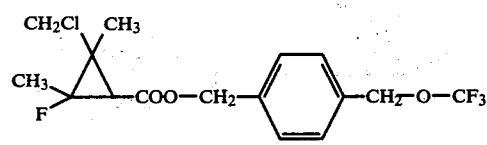 (19)

4'-Trifluoromethoxymethylbenzyl 2-chloromethyl-3-fluoro-2,3-dimethylcyclopropanecarboxylate, $n_D^{20}$ 1.5291

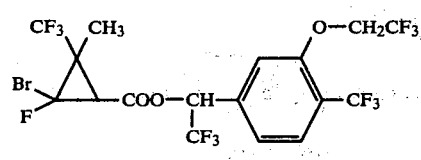 (20)

3'-(2,2,2-Trifluoroethoxy)-4'-trifluoromethyl-α'-trifluoromethylbenzyl 2-methyl-2-trifluoromethyl-3-bromo-3-fluorocyclopropanecarboxylate, $n_D^{20}$ 1.5408

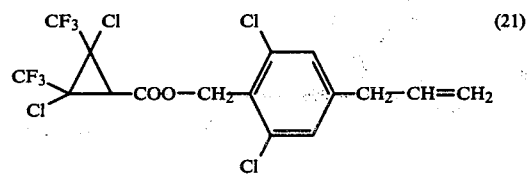 (21)

2',6'-Dichloro-4-allylbenzyl 2,3-dichloro-2,3-ditrifluoromethylcyclopropanecarboxylate, $n_D^{20}$ 1.5492

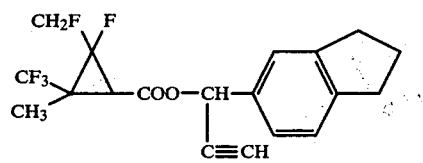 (22)

3',4'-Trimethylene-α'-ethynylbenzyl 2-fluoro-2-fluoromethyl-3-methyl-3-trifluoromethylcyclopropanecarboxylate, $n_D^{20}$ 1.5468

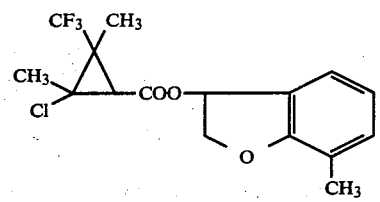 (23)

7'-Methyl-2',3'-dihydrobenzofuran-3'-yl 2-trifluoromethyl-3-chloro-2,3-dimethylcyclopropanecarboxylate, $n_D^{20}$ 1.5527

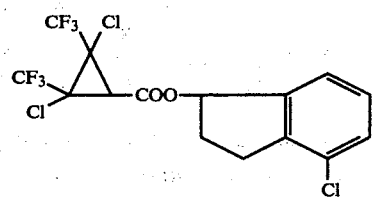 (24)

7'-Chloroindane-3'-yl 2,3-dichloro-2,3-ditrifluoromethylcyclopropanecarboxylate, $n_D^{20}$ 1.5530

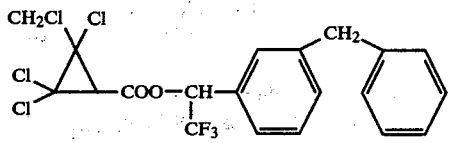 (25)

3'-Benzyl-α'-trifluoromethylbenzyl 2-chloromethyl-2,3,3-trichlorocyclopropanecarboxylate, $n_D^{20}$ 1.5714

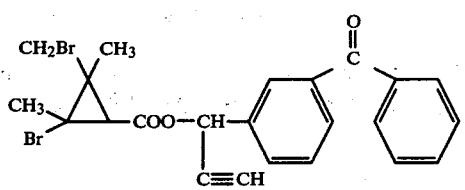 (26)

3'-Benzoyl-α'-ethynylbenzyl 2-bromomethyl-3-bromo-2,3-dimethylcyclopropanecarboxylate, $n_D^{20}$ 1.5765

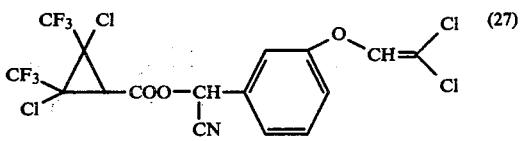 (27)

3'-(2,2-dichlorovinyloxy)-α'-cyanobenzyl 2,3-dichloro-2,3-ditrifluoromethylcyclopropanecarboxylate, $n_D^{20}$ 1.5610

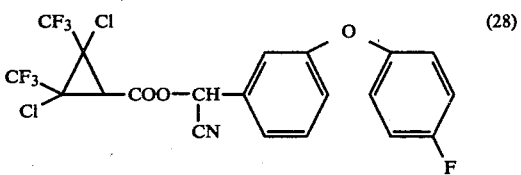 (28)

3'-(4-fluorophenoxy)-α'-cyanobenzyl 2,3-dichloro-2,3-ditrifluoromethylcyclopropanecarboxylate, $n_D^{20}$ 1.5451

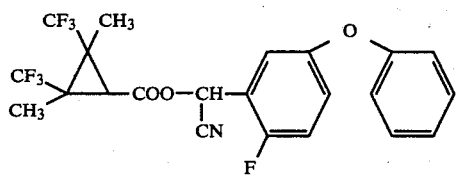

3'-Phenoxy-5'-fluoro-α'-cyanobenzyl 2,3-dimethyl-2,3-ditrifluoromethylcyclopropanecarboxylate, $n_D^{20}$ 1.5413

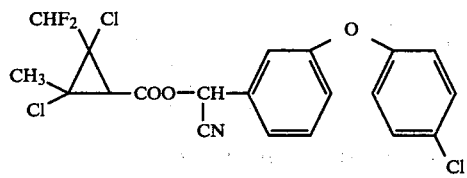

3'-(4-Chlorophenoxy)-α'-cyanobenzyl 2-difluoromethyl-3-methyl-2,3-dichlorocyclopropanecarboxylate, $n_D^{20}$ 1.5437

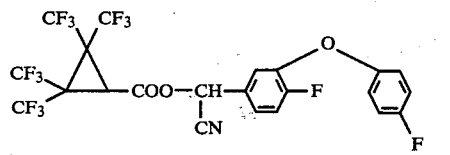

3'-(4-Fluorophenoxy)-4'-fluoro-α'-cyanobenzyl tetratrifluoromethylcyclopropanecarboxylate, $n_D^{20}$ 1.5396

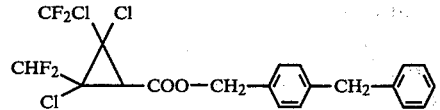

4'-Benzylbenzyl 2-difluorochloromethyl-3-difluoromethyl-2,3-dichlorocyclopropanecarboxylate, $n_D^{20}$ 1.5664

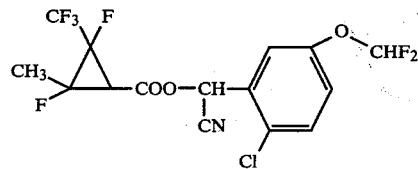

3'-Difluoromethoxy-6'-chloro-α'-cyanobenzyl 2-trifluoromethyl-3-methyl-2,3-difluorocyclopropanecarboxylate, $n_D^{20}$ 1.5263

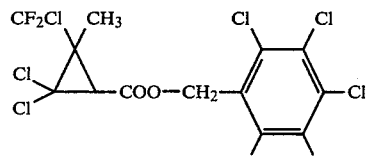

2',3',4',5',6'-Pentachlorobenzyl 2-methyl-2-difluorochloromethyl-3,3-dichlorocyclopropanecarboxylate, $n_D^{20}$ 1.5715

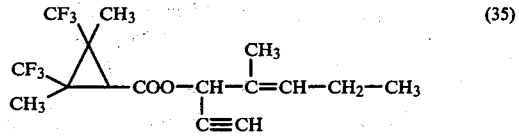

1'-Ethynyl-2'-methyl-2'-pentene-1'-yl 2,3-dimethyl-2,3-ditrifluoromethylcyclopropanecarboxylate, $n_D^{20}$ 1.4938

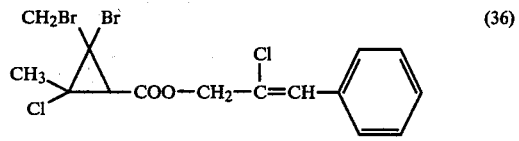

2'-Chloro-3'-phenylallyl 2-bromomethyl-2-bromo-3-methyl-3-chlorocyclopropanecarboxylate, $n_D^{20}$ 1.5426

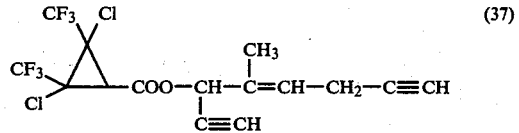

1'-Ethynyl-2'-methyl-3'-propargylallyl-1'-yl 2,3-dichloro-2,3-ditrifluoromethylcyclopropanecarboxylate, $n_D^{20}$ 1.5087

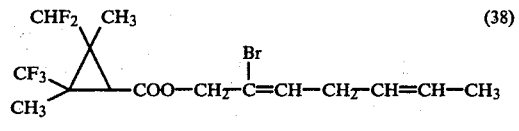

2'-Bromo-2',5'-heptadiene-1'-yl 2-difluoromethyl-3-trifluoromethyl-2,3-dimethylcyclopropanecarboxylate, $n_D^{20}$ 1.5203

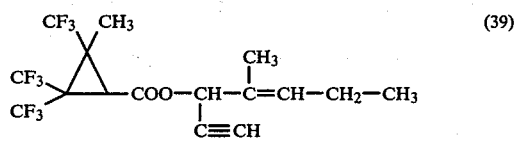

1'-Ethynyl-2'-methyl-2'-pentene-1'-yl 2-methyl-2,3,3-tritrifluoromethylcyclopropanecarboxylate, $n_D^{20}$ 1.4971

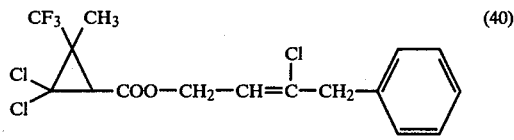

4'-Phenyl-3'-chloro-2'-butene-1'-yl 2-methyl-2-trifluoromethyl-3,3-dichlorocyclopropanecarboxylate, $n_D^{20}$ 1.5429

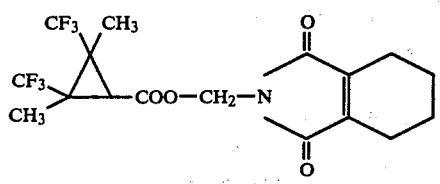 (41)

3',4',5',6'-Tetrahydrophthalimidemethyl 2,3-dimethyl-2,3-ditrifluoromethylcyclopropanecarboxylate, $n_D^{20}$ 1.5419

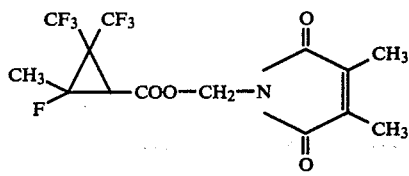 (42)

Dimethylmaleimidemethyl 2,2-ditrifluoromethyl-3-methyl-3-fluorocyclopropanecarboxylate, $n_D^{20}$ 1.5420

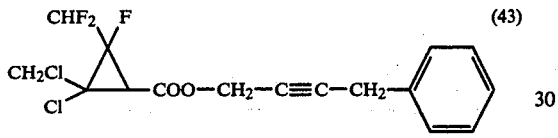 (43)

4'-Phenyl-2'-butyne-1'-yl 2-fluoro-2-difluoromethyl-3-chloro-3-chloromethylcyclopropanecarboxylate, $n_D^{20}$ 1.5367

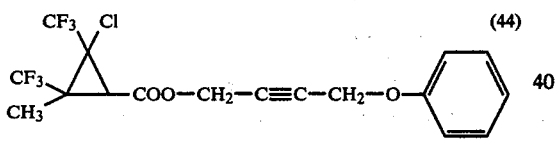 (44)

4'-Phenoxy-2'-butyne-1'-yl 2-chloro-3-methyl-2,3-ditrifluoromethylcyclopropanecarboxylate, $n_D^{20}$ 1.5380

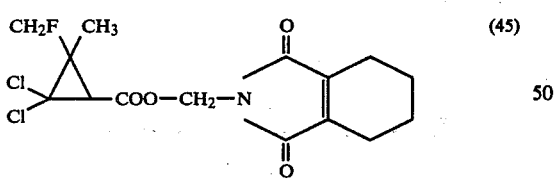 (45)

3',4',5',6'-Tetrahydrophthalimidemethyl 2-methyl-2-fluoromethyl-3,3-dichlorocyclopropanecarboxylate, $n_D^{20}$ 1.5465

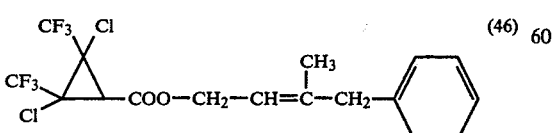 (46)

4'-Phenyl-3'-methyl-2'-butene-1'-yl 2,3-dichloro-2,3-ditrifluoromethylcyclopropanecarboxylate, $n_D^{20}$ 1.5405

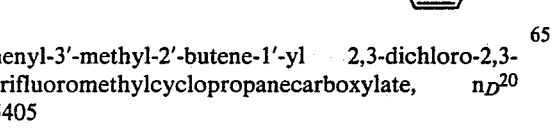 (47)

7'-Trifluoromethyl-2',3'-dihydrobenzofuran-3'-yl 2,2-difluoromethyl-3-methyl-3-chlorocyclopropanecarboxylate, $n_D^{20}$ 1.5412

(48)

2',6'-Dimethyl-4'-propargylbenzyl 2,3-dimethyl-2,3-ditrifluoromethylcyclopropanecarboxylate, $n_D^{20}$ 1.5351

(49)

3'-(3-Bromobenzoyl)-α'-propynylbenzyl 2-chloromethyl-2-difluoromethyl-3,3-dibromocyclopropanecarboxylate, $n_D^{20}$ 1.5822

(50)

5'-Propargyl-2'-furylmethyl 2,3-dimethyl-2,3-difluoromethylcyclopropanecarboxylate, $n_D^{20}$ 1.5173

(51)

2'-Allyl-3'-methyl-2'-cyclopentene-1'-one-4'-yl 2,2,3,3-tetrafluoromethylcyclopropanecarboxylate, $n_D^{20}$ 1.5209

(52)

2',3',4',5',6'-Pentafluorobenzyl 2,3-dichloro-2,3-ditrifluoromethylcyclopropanecarboxylate, $n_D^{20}$ 1.5327

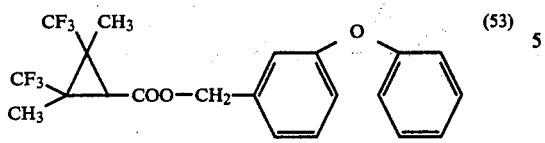
(53)

3'-Phenoxybenzyl 2,3-dimethyl-2,3-ditrifluoromethylcyclopropanecarboxylate, $n_D^{20}$ 1.5341

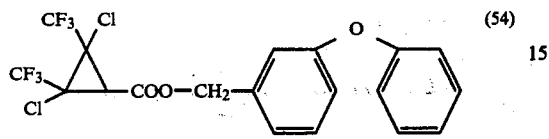
(54)

3'-Phenoxybenzyl 2,3-dichloro-2,3-ditrifluoromethylcyclopropanecarboxylate, $n_D^{20}$ 1.5375

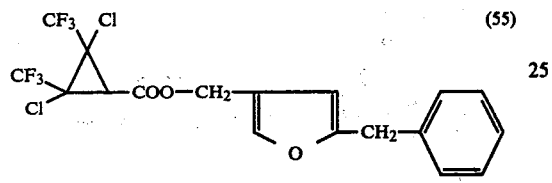
(55)

5'-Benzyl-3'-furylmethyl 2,3-dichloro-2,3-ditrifluoromethylcyclopropanecarboxylate, $n_D^{20}$ 1.5696

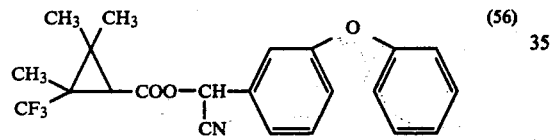
(56)

3'-Phenoxy-α'-cyanobenzyl 2,2,3-trimethyl-3-trifluoromethylcyclopropanecarboxylate, $n_D^{20}$ 1.5405

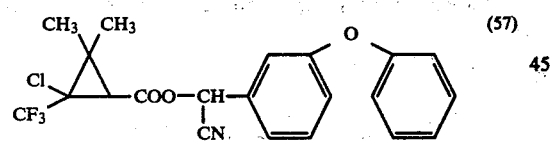
(57)

3'-Phenoxy-α'-cyanobenzyl 2,2-dimethyl-3-chloro-3-trifluoromethylcyclopropanecarboxylate, $n_D^{20}$ 1.5436

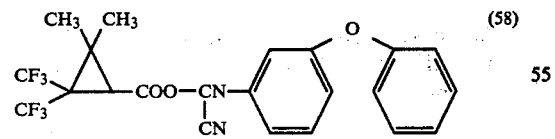
(58)

3'-Phenoxy-α'-cyanobenzyl 2,2-dimethyl-3,3-ditrifluoromethylcyclopropanecarboxylate, $n_D^{20}$ 1.5412

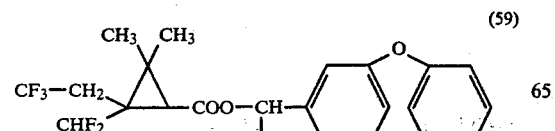
(59)

3'-Phenoxy-α'-cyanobenzyl 2,2-dimethyl-3-difluoromethyl-3-(2,2,2-trifluoroethyl)cyclopropanecarboxylate, $n_D^{20}$ 1.5487

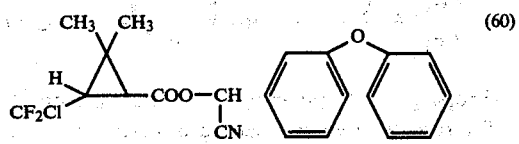
(60)

3'-Phenoxy-α'-cyanobenzyl 2,2-dimethyl-3-chlorodifluoromethylcyclopropanecarboxylate, $n_D^{20}$ 1.5465

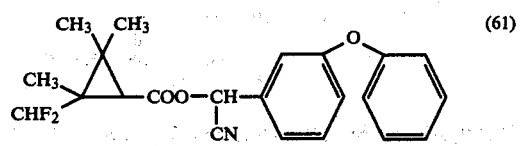
(61)

3'-Phenoxy-α'-cyanobenzyl 2,2,3-trimethyl-3-difluoromethylcyclopropanecarboxylate, $n_D^{20}$ 1.5423

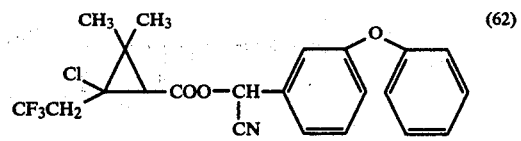
(62)

3'-Phenoxy-α'-cyanobenzyl 2,2-dimethyl-3-chloro-3-(2,2,2-trifluoroethyl)cyclopropanecarboxylate, $n_D^{20}$ 1.5510

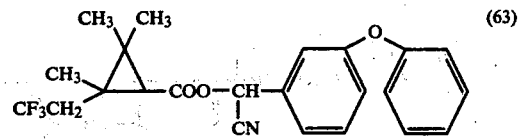
(63)

3'-Phenoxy-α'-cyanobenzyl 2,2,3-trimethyl-3-(2,2,2-trifluoroethyl)cyclopropanecarboxylate, $n_D^{20}$ 1.5481

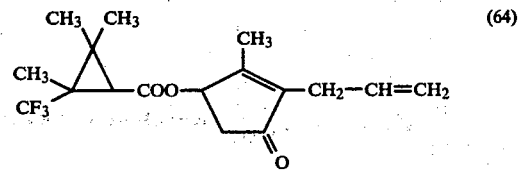
(64)

2'-Allyl-3'-methyl-2'-cyclopentene-1'-one-4'-yl 2,2,3-trimethyl-3-trifluoromethylcyclopropanecarboxylate, $n_D^{20}$ 1.5240

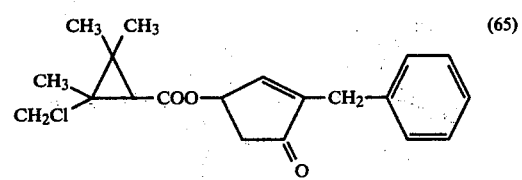
(65)

2'-Benzyl-2'-cyclopentene-1'-one-4'-yl 2,2,3-trimethyl-3-chloromethylcyclopropanecarboxylate, $n_D^{20}$ 1.5517

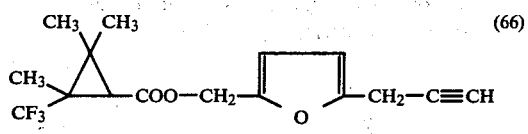

(66)

5'-Propargyl-2'-furylmethyl 2,2,3-trimethyl-3-trifluoromethylcyclopropanecarboxylate, $n_D^{20}$ 1.5204

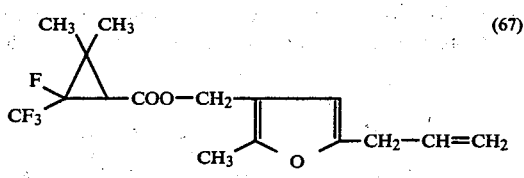

(67)

5'-Allyl-2'-methyl-3'furylmethyl 2,2-dimethyl-3-fluoro-3-trifluoromethylcyclopropanecarboxylate, $n_D^{20}$ 1.5233

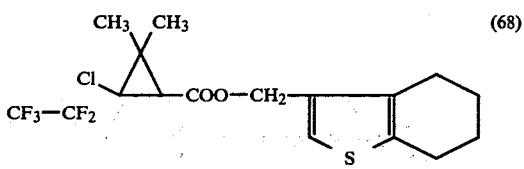

(68)

4',5'-Tetramethylene-3'-thenyl 2,2-dimethyl-3-chloro-3-(2,2,2,1,1-pentafluoroethyl)cyclopropanecarboxylate, $n_D^{20}$ 1.5429

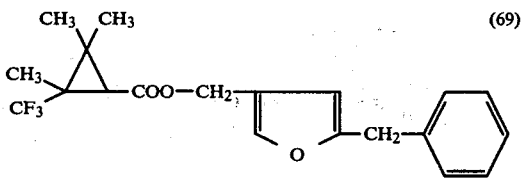

(69)

5'-Benzyl-3'-furylmethyl 2,2,3-trimethyl-3-trifluoromethylcyclopropanecarboxylate, $n_D^{20}$ 1.5492

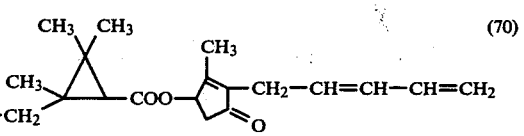

(70)

2'(2,4-Pentadienyl)-3'-methyl-2'-cyclopentene-1'-one-4'-yl 2,2,3-trimethyl-3-(2,2,2-trifluoroethyl)cyclopropanecarboxylate, $n_D^{20}$ 1.5386

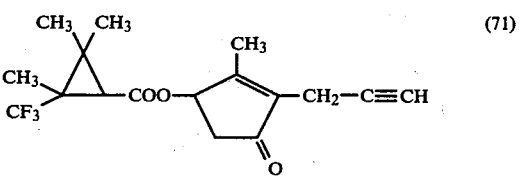

(71)

2'-Propargyl-3'-methyl-2'-cyclopentene-1'-one-4'-yl 2,2,3-trimethyl-3-trifluoromethylcyclopropanecarboxylate, $n_D^{20}$ 1.5264

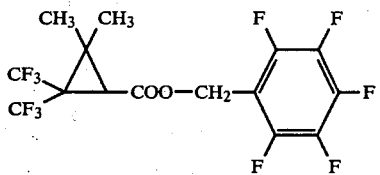

(72)

2',3',4',5',6'-Pentafluorobenzyl 2,2-dimethyl-3,3-ditrifluoromethylcyclopropanecarboxylate, $n_D^{20}$ 1.5271

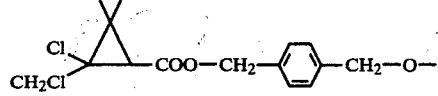

(73)

4'(2,2,2-Trifluoroethoxymethyl)benzyl 2,2-dimethyl-3-chloro-3-chloromethylcyclopropanecarboxylate, $n_D^{20}$ 1.5366

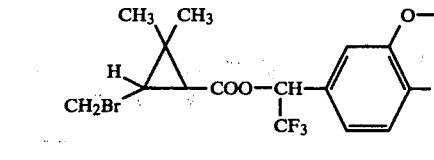

(74)

3'(2,2,2-Trifluoroethoxy)-4'-trifluoromethyl-α'-trifluoromethylbenzyl 2,2-dimethyl-3-bromomethyl cyclopropanecarboxylate, $n_D^{20}$ 1.5405

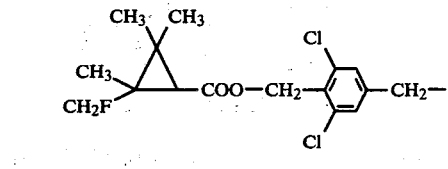

(75)

2',6'-Dichloro-4'-allylbenzyl 2,2,3-trimethyl-3-fluoromethylcyclopropanecarboxylate, $n_D^{20}$ 1.5487

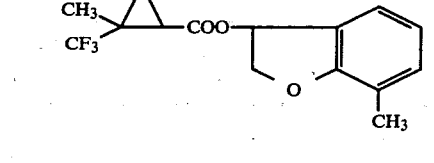

(76)

7'-Methyl-2',3'-dihydrobenzofuran-3'-yl 2,2,3-trimethyl-3-trifluoromethylcyclopropanecarboxylate, $n_D^{20}$ 1.5536

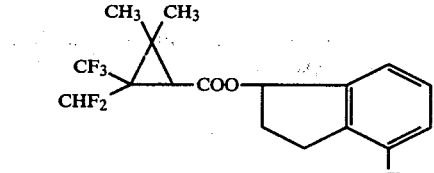

(77)

7'-Chlorindane-3'-yl 2,2-dimethyl-3-difluoromethyl-3-trifluoromethylcyclopropanecarboxylate, $n_D^{20}$ 1.5529

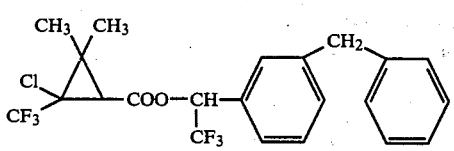

3′-Benzyl-α′-trifluoromethylbenzyl 2,2-dimethyl-3-chloro-3-trifluoromethylcyclopropanecarboxylate, $n_D^{20}$ 1.5615 (78)

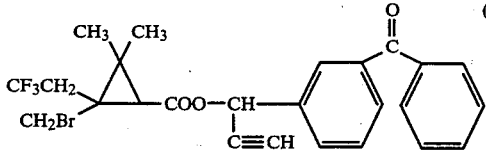

3′-Benzoyl-α′-ethynylbenzyl 2,2-dimethyl-3-bromomethyl-3-(2,2,2-trifluoroethyl)cyclopropanecarboxylate, $n_D^{20}$ 1.5703 (79)

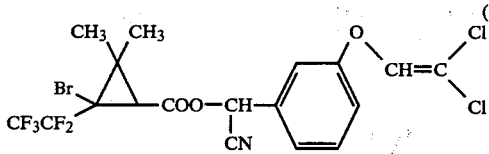

3′-(2,2-Dichlorovinyloxy)-α′-cyanobenzyl 2,2-dimethyl-3-bromo-3-(2,2,2,1,1-pentafluoroethyl)cyclopropanecarboxylate, $n_D^{20}$ 1.5628 (80)

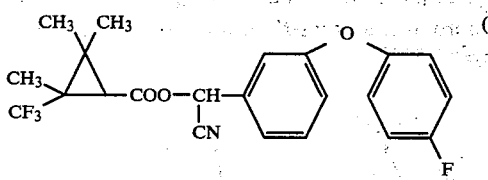

3′-(4-Fluorophenoxy)-α′-cyanobenzyl 2,2,3-trimethyl-3-trifluoromethylcyclopropanecarboxylate, $n_D^{20}$ 1.5420 (81)

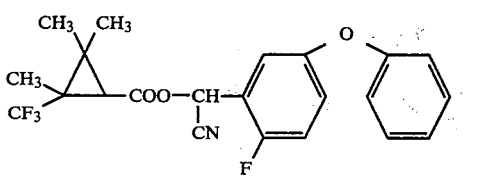

3′-Phenoxy-6′-fluoro-α′-cyanobenzyl 2,2,3-trimethyl-3-trifluoromethylcyclopropanecarboxylate, $n_D^{20}$ 1.5417 (82)

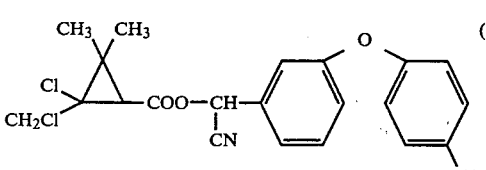

(83)

3′-(4-Chlorophenoxy)-α′-cyanobenzyl 2,2-dimethyl-3-chloro-3-chloromethylcyclopropanecarboxylate, $n_D^{20}$ 1.5449

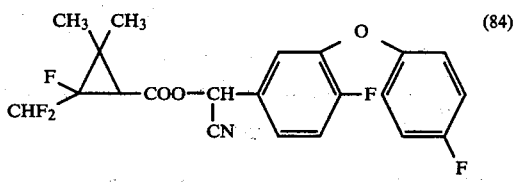

3′-(4-Fluorophenoxy)-4′-fluoro-α′-cyanobenzyl 2,2-dimethyl-3-fluoro-3-difluoromethylcyclopropanecarboxylate, $n_D^{20}$ 1.5376 (84)

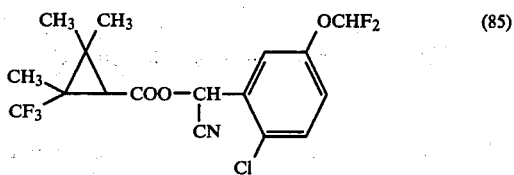

3′-Difluoromethoxy-6′-chloro-α′-cyanobenzyl 2,2,3-trimethyl-3-trifluoromethylcyclopropanecarboxylate, $n_D^{20}$ 1.5314 (85)

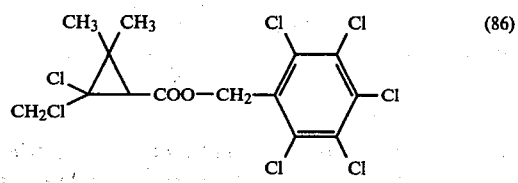

2′,3′,4′,5′,6′-Pentachlorobenzyl 2,2-dimethyl-3-chloro-3-chloromethylcyclopropanecarboxylate, $n_D^{20}$ 1.5683 (86)

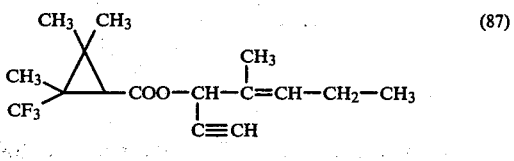

1′-Ethynyl-2′-methyl-2′-pentene-1′-yl 2,2,3-trimethyl-3-trifluoromethylcyclopropanecarboxylate, $n_D^{20}$ 1.4970 (87)

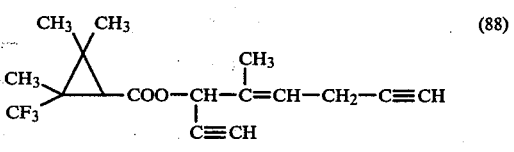

1′-Ethynyl-2′-methyl-3′-propargyl-1′-yl 2,2,3-trimethyl-3-trifluoromethylcyclopropanecarboxylate, $n_D^{20}$ 1.5012 (88)

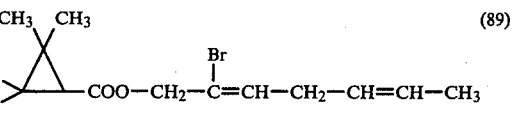
(89)

2'-Bromo-2',5'-heptadiene-1'-yl 2,2-dimethyl-3-chloro-3-difluoromethylcyclopropanecarboxylate, $n_D^{20}$ 1.5241

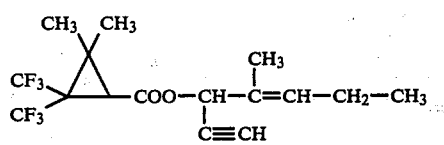
(90)

1'-Ethynyl-2'-methyl-2'-pentene-1'-yl 2,2,-dimethyl-3,3-ditrifluoromethylcyclopropanecarboxylate, $n_D^{20}$ 1.4939

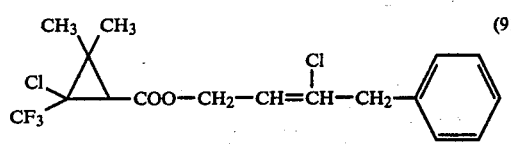
(91)

4'-Phenyl-3'-chloro-2'-butene-1'yl 2,2-dimethyl-3-chloro-3-trifluoromethylcyclopropanecarboxylate, $n_D^{20}$ 1.5405

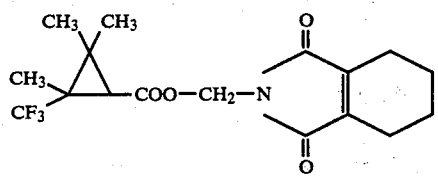
(92)

3',4',5',6'-Tetrahydrophthalimidemethyl 2,2,3-trimethyl-3-trifluoromethylcyclopropanecarboxylate, $n_D^{20}$ 1.5426

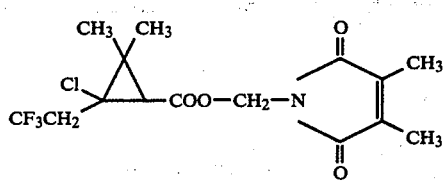
(93)

Dimethylmaleimidemethyl 2,2-dimethyl-3-chloro-3-(2,2,2-trifluoroethyl)cyclopropanecarboxylate, $n_D^{20}$ 1.5430

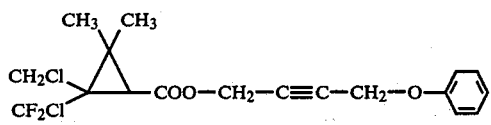
(94)

4'-Phenoxy-2'-butyne-1'yl 2,2-dimethyl-3-chloromethyl-3-chlorodifluoromethylcyclopropanecarboxylate, $n_D^{20}$ 1.5403

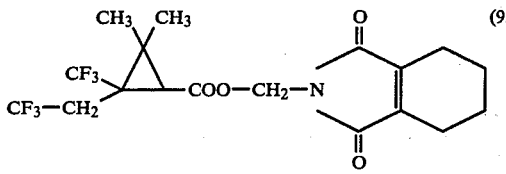
(95)

3',4',5',6'-Tetrahydrophthalimidemethyl 2,2-dimethyl-3-trifluoromethyl-3-(2,2,2-trifluoroethyl)cyclopropanecarboxylate, $n_D^{20}$ 1.5454

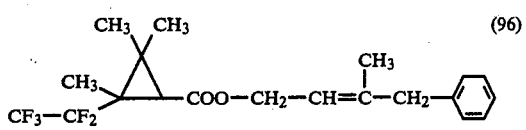
(96)

4'-Phenyl-3'-methyl-2'-butene-1'-yl 2,2,3-trimethyl-3-(2,2,2,1,1-pentafluoroethyl)cyclopropanecarboxylate, $n_D^{20}$ 1.5395

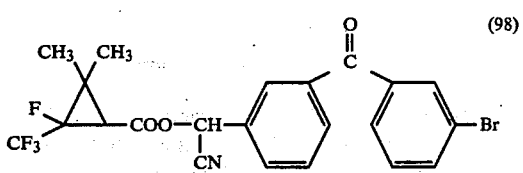
(97)

7'-Trifluoromethyl-2',3'-dihydrobenzofuran-3'-yl 2,2-dimethyl-3-difluoromethylcyclopropanecarboxylate, $n_D^{20}$ 1.5418

(98)

3'-(3-Bromobenzoyl)-α'-cyanobenzyl 2,2-dimethyl-3-fluoro-3-trifluoromethylcyclopropanecarboxylate, $n_D^{20}$ 1.5678

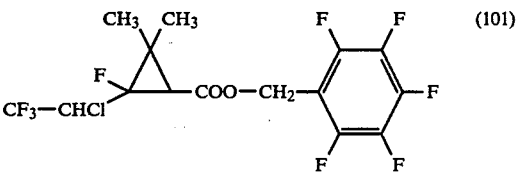
(99)

5'-Propargyl-2'-furylmethyl 2,2-dimethyl-3,3-ditrifluoromethylcyclopropanecarboxylate, $n_D^{20}$ 1.5211

(100)

2'-Allyl-3'-methyl-2'-cyclopentene-1'-one-4'-yl 2,2-dimethyl-3,3-ditrifluoromethylcyclopropanecarboxylate, $n_D^{20}$ 1.5245

(101)

2',3',4',5',6'-Pentafluorobenzyl 2,2-dimethyl-3-fluoro-3-(1-chloro-2,2,2-trifluoromethyl)cyclopropanecarboxylate, $n_D^{20}$ 1.5304

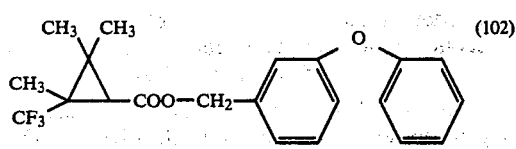

3'-Phenoxybenzyl 2,2,3-trimethyl-3-trifluoromethylcyclopropanecarboxylate, $n_D^{20}$ 1.5356

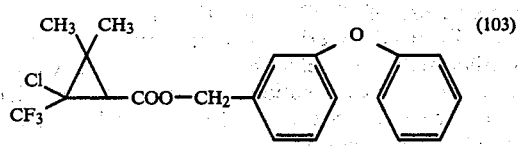

3'-Phenoxybenzyl 2,2-dimethyl-3-chloro-3-trifluoromethylcyclopropanecarboxylate, $n_D^{20}$ 1.5329

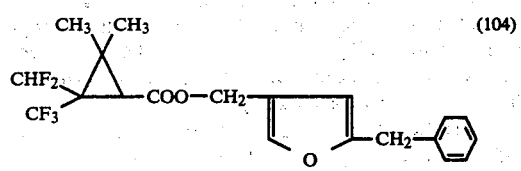

5'-Benzyl-3'-furylmethyl 2,2-dimethyl-3-difluoromethyl-3-trifluoromethylcyclopropanecarboxylate, $n_D^{20}$ 1.5470

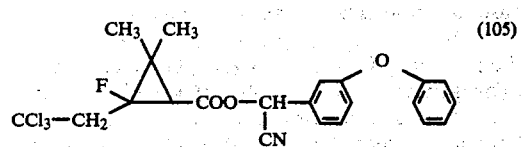

3'-Phenoxy-α'-cyanobenzyl 2,2-dimethyl-3-fluoro-3-(2,2,2-trichloroethyl)cyclopropanecarboxylate, $n_D^{20}$ 1.5590

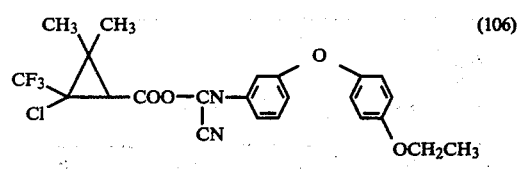

3'(4-Ethoxyphenoxy)-α'-cyanobenzyl 2,2-dimethyl-3-trifluoromethyl-3-chlorocyclopropanecarboxylate, $n_D^{20}$ 1.5412

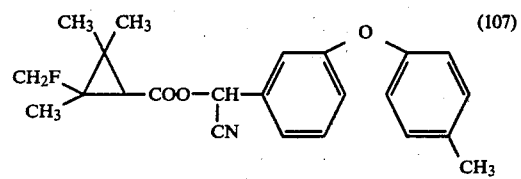

3'-(4-Methylphenoxy)-α'-cyanobenzyl 2,2,3-trimethyl-3-fluoromethylcyclopropanecarboxylate, $n_D^{20}$ 1.5405

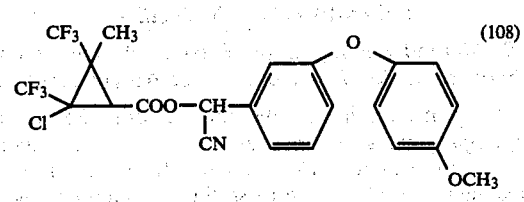

3'-(4-Methoxyphenoxy)-α'-cyanobenzyl 2-methyl-2,3-ditrifluoromethyl-3-chlorocyclopropanecarboxylate, $n_D^{20}$ 1.5396

The method of manufacturing the esters according to this invention will now be described in detail with reference to examples of synthesis.

EXAMPLE OF SYNTHESIS 1

A. Method Employing the Reaction between an Alcohol and a Carboxylic Acid Halide A solution containing 3.7 g of 5-benzyl-3-furylmethyl alcohol in 20 ml of dry benzene was added into a solution containing 5.4 g of 2,3-dimethyl-2,3-ditrifluoromethylcyclopropanecarboxylic acid chloride in 15 ml of dry benzene. Then, 3 ml of dry pyridine were added into the mixed solution as a condensation assistant, whereby pyridine hydrochloride crystals were precipitated. The reactor was closed tightly, and after it had been left to stand overnight at room temperature, the crystals were separated by filtration, and the benzene solution was dried over Glauber's salt and benzene was distilled off in vacuum, whereby there were obtained 7.1 g of 5'-benzyl-3'-furylmethyl 2,3-dimethyl-2,3-ditrifluoromethylcyclopropanecarboxylate.

EXAMPLE OF SYNTHESIS 2

B. Method Employing the Reaction between an Alcohol and a Carboxylic Acid 6.0 g of 2,3-dichloro-2,3-ditrifluoromethylcyclopropanecarboxylic acid, and 3.3 g of 4-phenyl-3-methyl-2-butene-1-ol were dissolved in 50 ml of dry benzene. 62 g of dicyclohexylcarbodiimide were added into the solution, and the solution was left to stand overnight in a tightly closed container. On the following day, the solution was heated under reflux for four hours, and the reaction was completed. The reaction product was cooled, and the precipitated dicyclohexyl urea was separated by filtration. An oily substance was obtained by concentration of the filtrate, and caused to flow down through a column of 100 g of silica gel to yield 7.2 g of 4'-phenyl-3'-methyl-2'-butene-1'-yl 2,3-dichloro-2,3-ditrifluoromethylcyclopropanecarboxylate.

EXAMPLE OF SYNTHESIS 3

C. Method Employing the Reaction between an Alcohol Halide and an Alkali Metal Carboxylate 5.5 g of sodium 2,2-ditrifluoromethyl-3-methyl-3-fluorocyclopropanecarboxylate, and 3.5 g of dimethylmaleimidemethyl chloride were suspended in 50 ml of benzene. The suspension was subjected to three hours of reaction under reflux in a nitrogen gas stream. After the reaction product had been carefully washed with a saline solution, it was dried over Glauber's salt for removal of benzene by vacuum distillation to yield 6.1 g of dimethylmaleimidemethyl 2,2-ditrifluoromethyl-3-methyl-3-fluorocyclopropanecarboxylate.

EXAMPLE OF SYNTHESIS 4

D. Method Employing the Ester Exchange Reaction between an Alcohol and a Lower Alkyl Carboxylate 6.3 g of a methyl 2,3-dichloro-2,3-ditrifluoromethyl-cyclopropanecarboxylate, and 3.2 g of 7-chloro-indane-3-ol were heated to 150° C. When the temperature had reached 150° C., 0.25 g of sodium was added, and the removal of methanol by distillation was started. After the distillation of methanol had stopped, 0.25 g of sodium was added again. These procedures were repeated until a theoretical quantity of methanol was obtained, while the temperature of around 150° C. was maintained. Then, the mixture was cooled, and dissolved in ether. The ether solution was washed with diluted hydrochloric acid, with a sodium bicarbonate solution and with a saline solution. It was dried over Glauber's salt, and the ether was removed by vacuum distillation, whereby there were obtained 7.1 g of 7'-chloroindane-3'-yl 2,3-dichloro-2,3-ditrifluoromethylcyclopropanecarboxylate.

EXAMPLE OF SYNTHESIS 5

E. Method Employing the Reaction between an Alcohol and a Carboxylic Acid Anhydride 7.5 g of 2,2,3-trimethyl-3-trifluoromethycyclopropanecarboxylic acid anhydride, and 3.1 g of 2-propargyl-3-methyl-2-cyclopentene-1-one-4-ol were dissolved in 50 ml of dry pyridine. They were left to stand overnight at ordinary room temperature, while being stirred. On the following day, the reaction solution was poured into 100 g of ice water, and extracted three times with 20 ml of ether. The ether layers were combined, and extracted twice with 20 ml of a 5% aqueous solution of sodium hydroxide, whereby the carboxylic acid, which had formed as a by-product, was removed. Then, the ether layer was washed with dilute hydrochloric acid, with a sodium bicarbonate solution and with a saline solution. It was dried over Glauber's salt, and the ether was removed under reduced pressure, whereby a crude ester was obtained. The crude ester was caused to flow down through a column of 20 g of activated alumina to yield 6.0 g of 2'-propargyl-3'-methyl-2'-cyclopentene-1'-one-4'-yl 2,2,3-trimethyl-3-trifluoromethylcyclopropanecarboxylate.

EXAMPLE OF SYNTHESIS 6

F. Method Employing the Reaction between an Alcohol Halide and the Carboxylic Acid Salt of an Organic Tertiary Base 4.4 g of 2-difluoromethyl-3-methyl-2,3-dichlorocyclopropanecarboxylic acid were dissolved in 50 ml of acetone, and 6.4 g of 3-(4-chlorophenoxy)-α-cyanobenzyl bromide were added thereinto. After 4 ml of triethylamine had been added into the solution while it was being stirred, they were reacted for three hours at a temperature of 60° C. to 80° C. The reaction product was dissolved in ether, and the ether solution was washed fully with dilute hydrochloric acid, with a sodium bicarbonate solution and with a saline solution. Then, the solution was dried over Glauber's salt, and the ether was removed by vacuum distillation, whereby there were obtained 7.2 g of 3'-(4-chlorophenoxy)-2'-cyanobenzyl 2-difluoromethyl-3-methyl-2,3-dichlorocyclopropanecarboxylate.

The compounds shown in the following table were also obtained in accordance with the methods employed in Examples of Synthesis 1 to 6. In the table, the symbols (a) to (e) indicating the method of esterification have the following meanings:

a. Method employing the reaction between an alcohol and a carboxylic acid halide (Example 1);

b. Dehydroesterification between an acid and an alcohol by dicyclohexylcarbodiimide in an inert solvent (Example 2);

c. Method employing the reaction between an alcohol halide, and an alkali metal, silver or organic tertiary base salt of an acid (Examples 3 and 6);

d. Method employing an ester exchange reaction in the presence of an alkali metal, alkali metal alkoxide or hydrogenated sodium catalyst (Example 4); and e. Method employing the reaction between an alcohol and a carboxylic acid anhydride (Example 5).

In connection with the elemental analysis shown in the table, the word "actual" means the value obtained by actual measurement, and the word "calculated" means the value obtained by calculation.

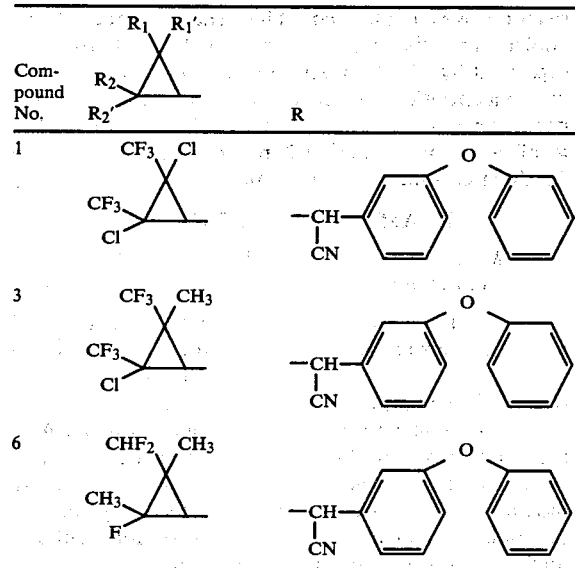

| Compound No. | $R_1$ $R_1'$ $R_2$ $R_2'$ | R | Method for esterification | Yield (%) | Elemental analysis C, H, N | |
|---|---|---|---|---|---|---|
| 1 | $CF_3$, $Cl$ / $CF_3$, $Cl$ | —CH(CN)—O—Ph—Ph | c | 86 | Found: 48.43, 2.19, 2.78 Calculated: 48.21, 2.23, 2.81 | $C_{20}H_{11}NO_3Cl_2F_6$ |
| 3 | $CF_3$, $CH_3$ / $CF_3$, $Cl$ | —CH(CN)—O—Ph—Ph | a | 88 | Found: 52.63, 2.97, 2.91 Calculated: 52.78, 2.96, 2.93 | $C_{21}H_{14}NO_3ClF_6$ |
| 6 | $CHF_2$, $CH_3$ / $CH_3$, $F$ | —CH(CN)—O—Ph—Ph | b | 82 | Found: 64.70, 4.69, 3.51 Calculated: 64.77, 4.67, 3.60 | $C_{21}H_{18}NO_3F_3$ |

-continued

| Compound No. | R₁ R₁' / R₂ R₂' (cyclopropane substituents) | R | Method for esterification | Yield (%) | Elemental analysis Found / Calculated: C, H, N | Formula |
|---|---|---|---|---|---|---|
| 9 | R₁=CF₃, R₁'=CH₃, R₂=CF₃, R₂'=CH₃ | 3-methyl-2-(prop-2-enyl)-4-oxocyclopent-2-enyl (—CH with CH₃, CH₂—CH=CH₂, =O) | a | 90 | Found: 53.38, 4.54, —<br>Calculated: 53.12, 4.73, — | $C_{17}H_{18}O_3F_6$ |
| 11 | R₁=CF₃, R₁'=CH₃, R₂=CF₃, R₂'=CH₃ | —CH₂—(furan-2,5-diyl)—CH₂—C≡CH | b | 85 | Found: 52.35, 3.79, —<br>Calculated: 52.17, 3.84, — | $C_{16}H_{14}O_3F_6$ |
| 23 | R₁=CF₃, R₁'=CH₃, R₂=CH₃, R₂'=Cl | 7-methyl-2,3-dihydrobenzofuran-? | e | 75 | Found: 55.02, 4.67, —<br>Calculated: 55.10, 4.63, — | $C_{16}H_{16}O_3ClF_3$ |
| 27 | R₁=CF₃, R₁'=Cl, R₂=CF₃, R₂'=Cl | α-cyano-3-(2,2-dichlorovinyloxy)benzyl (—CH(CN)—C₆H₄—O—CH=CCl₂) | a | 90 | Found: 37.26, 1.30, 2.78<br>Calculated: 37.17, 1.37, 2.71 | $C_{16}H_7NO_3Cl_4F_6$ |
| 39 | R₁=CF₃, R₁'=CH₃, R₂=CF₃, R₂'=CF₃ | —CH(C≡CH)—C(CH₃)=CH—CH₂—CH₃ | b | 85 | Found: 46.74, 3.70, —<br>Calculated: 46.83, 3.69, — | $C_{16}H_{15}O_2F_9$ |
| 45 | R₁=CH₂F, R₁'=CH₃, R₂=Cl, R₂'=Cl | —CH₂—N(3,4,5,6-tetrahydrophthalimido) | c | 80 | Found: 49.52, 4.41, 3.89<br>Calculated: 49.46, 4.44, 3.85 | $C_{15}H_{16}NO_4Cl_2F$ |
| 52 | R₁=CF₃, R₁'=Cl, R₂=CF₃, R₂'=Cl | —CH₂—C₆F₅ (pentafluorobenzyl) | d | 78 | Found: 33.40, 0.59, —<br>Calculated: 33.14, 0.64, — | $C_{13}H_3O_2Cl_2F_{11}$ |
| 56 | R₁=CH₃, R₁'=CH₃, R₂=CH₃, R₂'=CF₃ | —CH(CN)—C₆H₄—O—C₆H₅ (α-cyano-3-phenoxybenzyl) | c | 87 | Found: 65.38, 5.07, 3.50<br>Calculated: 65.49, 5.01, 3.47 | $C_{22}H_{20}NO_3F_3$ |
| 57 | R₁=CH₃, R₁'=CH₃, R₂=Cl, R₂'=CF₃ | —CH(CN)—C₆H₄—O—C₆H₅ (α-cyano-3-phenoxybenzyl) | a | 90 | Found: 59.44, 4.09, 3.35<br>Calculated: 59.51, 4.05, 3.31 | $C_{21}H_{17}NO_3ClF_3$ |
| 68 | R₁=CH₃, R₁'=CH₃, R₂=Cl (with CF₃—CF₂ substituent) | —CH₂—(4,5,6,7-tetrahydrobenzo[b]thien-2-yl) | b | 81 | Found: 48.85, 4.41, —<br>Calculated: 48.98, 4.36, — | $C_{17}H_{18}O_2SClF_5$ |

-continued

| Compound No. | R₁, R₁', R₂, R₂' (cyclopropane) | R | Method for esterification | Yield (%) | Elemental analysis Found / Calculated: C, H, N | |
|---|---|---|---|---|---|---|
| 69 | R₁=CH₃, R₁'=CH₃, R₂=CH₃, R₂'=CF₃ | −CH₂−(furan-2-yl)−CH₂−phenyl | a | 86 | Found: 65.48, 5.83, — Calculated: 65.55, 5.79, — | $C_{20}H_{21}O_3F_3$ |
| 74 | R₁=CH₃, R₁'=CH₃, R₂=H, R₂'=CH₂Br | −CH(CF₃)−phenyl(−O−CH₂CF₃, −CF₃) | e | 80 | Found: 40.83, 3.01, — Calculated: 40.69, 3.04, — | $C_{18}H_{16}O_3BrF_9$ |
| 78 | R₁=CH₃, R₁'=CH₃, R₂=Cl, R₂'=CF₃ | −CH(CF₃)−phenyl−CH₂−phenyl | d | 76 | Found: 56.94, 4.06, — Calculated: 56.84, 4.13, — | $C_{22}H_{19}O_2ClF_6$ |
| 94 | R₁=CH₃, R₁'=CH₃, R₂=CH₂Cl, R₂'=CF₂Cl | −CH₂−C≡C−CH₂−O−phenyl | b | 82 | Found: 55.17, 4.69, — Calculated: 55.25, 4.65, — | $C_{18}H_{18}O_3Cl_2F_2$ |
| 98 | R₁=CH₃, R₁'=CH₃, R₂=F, R₂'=CF₃ | −CH(CN)−phenyl−C(=O)−phenyl−Br | c | 83 | Found: 52.95, 3.30, 2.88 Calculated: 53.03, 3.24, 2.81 | $C_{22}H_{16}NO_3BrF_4$ |
| 104 | R₁=CH₃, R₁'=CH₃, R₂=CHF₂, R₂'=CF₃ | −CH₂−(furan-2-yl)−CH₂−phenyl | b | 85 | Found: 59.80, 4.73, — Calculated: 59.69, 4.77, — | $C_{20}H_{19}O_3F_5$ |
| 105 | R₁=CH₃, R₁'=CH₃, R₂=F, R₂'=CCl₃CH₂ | −CH(CN)−phenyl−O−phenyl | c | 87 | Found: 56.27, 4.01, 2.96 Calculated: 56.13, 4.08, 2.98 | $C_{22}H_{19}NO_3Cl_3F$ |

The cyclopropanecarboxylic acids of the formula VIII, which are employed in this invention, may be prepared, as usual, by, for example:

(1) Reacting an alkene with ethyl diazoacetate, and hydrolyzing the reaction product, i.e.,

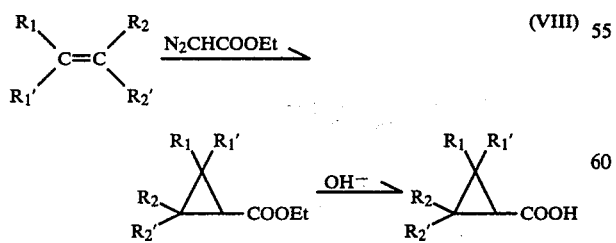

or (2) Adding chloroketene to an alkene to form cyclobutanone, and deriving a cyclopropanecarboxylic acid therefrom in the presence of a base, i.e.,

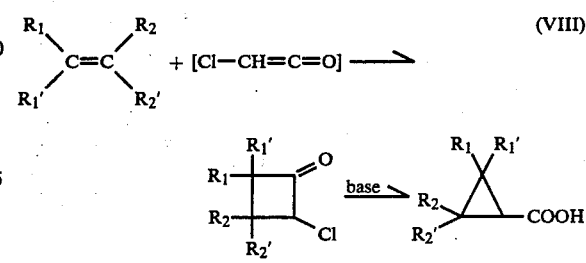

A Compound containing a fluorine atom in a substituent can be prepared through an ethyl ester of a corresponding cyclopropanecarboxylic acid containing chlorine or bromine atom being synthesized, and reacted with AgF, or the like for conversion to a fluorine compound.

The compounds of this invention are novel compounds which are solid or liquid at ordinary room temperature, and which are easily soluble in organic solvents in general. If they are employed for preparing an insecticide for use by spraying, therefore, they may take the form of an emulsifiable concentrate, an oily preparation, a powder preparation, a wettable powder, an aerosol, or the like. They can also be used for preparing an insecticide for use by fumigation, such as a mosquito-repellent incense, if they are mixed with an appropriate substrate, such as wooden dust. The compounds may also be useful in preparing a so-called electric mosquito repellent in the form of a solution in an appropriate solvent, or a paper base impregnated with a solution thereof in an appropriate organic solvent. The electric mosquito repellent may be heated by an appropriate heater, and vaporized. Moreover, they exhibit equally outstanding effects in repelling mosquitoes when vaporized by a chemical heater, or by employing a sublimable assistant such as adamantane, cyclododecane or trimethylenenorbornane. The chemical heater which generates heat when contacted with air or water may, for example, comprise a composition of sodium sulfide and carbon, a composition of salt, iron and carbon, a composition of salt, iron, carbon and sodium metasilicate, or unslaked lime.

The compounds of this invention are stable against light as compared with the known chrysanthemumic ester pyrethroid, have a wide insecticidal spectrum, can effectively kill the insects which are resistant to the known organic phosphorus or carbamate insecticides, have low degrees of toxicity, and are inexpensive. For these reasons, the compounds of this invention are very useful substitutes for the known organic phosphorus or chlorine insecticides for agricultural and gardening uses. The compounds of this invention are very useful for the extermination of hygenically harmful insects such as flies, mosquitoes, cockroaches, agriculturally harmful insects which are resistant to organic phosphorus or carbamate insecticides, such as green rice leaf hoppers, plant-hoppers, rice stem borers, bean bugs, cabbage armyworms, diamond-back moths, oriental tobacco budworms, seed beetles, owlet moths and underwings, common cabbage worms, Japanese giant silk moths, leaf rollers, aphids, mealy bugs and scale insects; rice weevils and other insects which are harmful to cereals in stock, mites, and the like. It is possible to enhance further the insecticidal action of the compounds according to this invention, when they are used with a synergist such as N-octylbicycloheptenedicarboxyimide, known under the trade name of MGK-264, a mixture thereof with an arylsulfonate known under the trade name of MGK-5026, N-octyl-1-isopropyl-4-methylbicyclo[2,2,2]octo-5-ene-2,3-dicarboxyimide, octachlorodipropylether, or piperonylbutoxide. It is also possible to increase the stability of the compounds according to this invention to a further extent by adding BHT, DBHQ, or the like as stabilizer or oxidation inhibitor thereto, if required. It is further possible to mix with the compounds of this invention other insecticides, including an organic phosphorus insecticide such as fenitrotion, DDVP, diazinon, propaphos, or pyridaphenthion, a carbamate such as NAC, MTMC, BPMC or PHC, a pyrethroid such as pyrethrin, allethrin, phthalthrin, furamethrin, phenothrin, permethrin, cypermethrin, decamethrin, fenevalerate or fenpropanate, other insecticides such as cartrap, chlorophenamidine or methomyl, an acaricide, a germicide, a nematocide, a herbicide, a plant growth regulator, a fertilizer, or other agrochemicals. The mixture provides a multipurpose composition which is outstandingly effective against harmful insects of the kind which resist an organic phosphorus or carbamate insecticide. The use of any such mixture contributes to saving the labor which is required for application of the individual chemicals, while it produces the synergistic effects of the individual chemicals.

The following is a description of the results of the tests conducted for ascertaining the light stability and the insecticidal and acaricidal effects of compositions according to this invention.

TESTS ON LIGHT STABILITY

About 50 mg of each of ten compounds which were selected from among the compounds of this invention as hereinbefore listed by way of example and the known pyrethroids as controls were spread in a thin layer on a glass laboratory dish having a diameter of 3 cm, and exposed to the sun light on a fine day in summer from 9 o'clock in the morning to 5 o'clock in the evening. After a certain length of time had passed, each compound was collected by washing with 50 ml of acetone. It was concentrated, and its residual percentage was obtained by gas chromatography. The following table shows the results:

| Compound tested | Compound residual rate (%) | | | | |
|---|---|---|---|---|---|
| | 1 day | 2 days | 3 days | 4 days | 5 days |
| Control compounds | | | | | |
| Allethrin | 43 | 22 | 4 | — | — |
| Resmethrin | 88 | 40 | 8 | — | — |
| Phenothrin | 92 | 72 | 54 | 27 | 5 |
| Compounds of the invention | | | | | |
| 2 | 95 | 93 | 88 | 83 | 78 |
| 4 | 93 | 90 | 85 | 80 | 74 |
| 18 | 94 | 90 | 83 | 78 | 75 |
| 27 | 95 | 92 | 89 | 85 | 80 |
| 46 | 94 | 89 | 86 | 80 | 73 |
| 51 | 92 | 80 | 73 | 51 | 34 |
| 57 | 96 | 92 | 88 | 84 | 79 |
| 73 | 94 | 90 | 84 | 79 | 73 |
| 97 | 95 | 88 | 83 | 78 | 71 |
| 103 | 95 | 91 | 86 | 82 | 77 |
| 108 | 96 | 91 | 85 | 81 | 79 |

As is obvious from the foreogoing table, the compounds of this invention have a far higher degree of stability against the sunlight, as compared with the known pyrethroids. This testifies that the compounds of this invention are very effective for outdoor use, and can maintain their effectiveness for a long period of time.

INSECTICIDAL TEST 1: Insecticidal Tests by Spraying

There were prepared a 0.2% kerosine solution of each of the compounds according to this invention, or allethrin or phthalthrin (control) (Group A), a kerosine solution containing 0.2% of each of the compounds according to this invention, and 0.8% of piperonyl butoxide (Group B), and a kerosine solution containing 0.1% of each compound according to this invention, and 0.1% of phthalthrin (Group C). With respect to each of the solutions thus prepared, the knockdown rate of houseflies was determined. Relative effectiveness of the test compounds was calculated taking the knockdown rate of allethrin as 1.00. The following table shows the mortality after 24 hours. In the table, the figures indicate the knockdown rates and those in the parentheses indicate the mortality after 24 hours.

| Compound tested | (A) | (B) | (C) |
|---|---|---|---|
| Control compounds | | | |
| Allethrin | 1.00 (26) | — | — |
| Phthalthrin | 2.15 (34) | — | — |
| Compounds of the invention | | | |
| (1) | 2.58 (100) | 4.52 (100) | 2.56 (100) |
| (2) | 2.65 (100) | 4.61 (100) | 2.60 (100) |
| (3) | 2.40 (100) | 4.39 (100) | 2.37 (100) |
| (4) | 2.39 (100) | 4.25 (100) | 2.40 (100) |
| (5) | 2.51 (100) | 4.43 (100) | 2.48 (100) |
| (6) | 2.28 (100) | 4.14 (100) | 2.35 (100) |
| (7) | 2.47 (100) | 4.56 (100) | 2.48 (100) |
| (8) | 2.44 (100) | 4.33 (100) | 2.37 (100) |
| (9) | 2.53 (100) | 4.57 (100) | 2.41 (100) |
| (10) | 1.61 (70) | 2.95 (94) | 1.97 (72) |
| (11) | 2.70 (100) | 4.65 (100) | 2.69 (100) |
| (12) | 2.16 (100) | 4.02 (100) | 2.24 (100) |
| (13) | 1.55 (65) | 2.86 (92) | 1.93 (72) |
| (14) | 1.48 (68) | 2.80 (88) | 1.90 (76) |
| (15) | 2.72 (100) | 4.79 (100) | 2.65 (100) |
| (16) | 2.86 (92) | 3.81 (100) | 2.18 (100) |
| (17) | 2.60 (100) | 4.47 (100) | 2.55 (100) |
| (18) | 2.19 (100) | 4.29 (100) | 2.24 (100) |
| (19) | 2.30 (100) | 4.36 (100) | 2.31 (100) |
| (20) | 1.85 (88) | 3.62 (100) | 2.08 (100) |
| (21) | 2.26 (100) | 4.13 (100) | 2.24 (100) |
| (22) | 1.81 (82) | 3.50 (100) | 2.16 (100) |
| (23) | 2.28 (100) | 4.31 (100) | 2.29 (100) |
| (24) | 2.17 (100) | 4.17 (100) | 2.20 (100) |
| (25) | 1.92 (84) | 3.85 (100) | 2.11 (100) |
| (26) | 1.64 (75) | 3.14 (94) | 2.03 (78) |
| (27) | 2.03 (92) | 3.95 (100) | 2.16 (100) |
| (28) | 2.52 (100) | 4.40 (100) | 2.50 (100) |
| (29) | 2.49 (100) | 4.41 (100) | 2.43 (100) |
| (30) | 2.40 (100) | 4.32 (100) | 2.42 (100) |
| (31) | 2.38 (100) | 4.39 (100) | 2.36 (100) |
| (32) | 1.65 (75) | 2.78 (94) | 1.99 (78) |
| (33) | 2.09 (100) | 3.90 (100) | 2.23 (100) |
| (34) | 1.96 (90) | 3.86 (100) | 2.14 (100) |
| (35) | 2.31 (100) | 4.16 (100) | 2.38 (100) |
| (36) | 1.44 (65) | 2.75 (90) | 1.87 (72) |
| (37) | 2.26 (100) | 4.04 (100) | 2.25 (100) |
| (38) | 1.52 (80) | 2.97 (100) | 1.95 (92) |
| (39) | 2.33 (100) | 4.12 (100) | 2.36 (100) |
| (40) | 2.25 (100) | 4.19 (100) | 2.27 (100) |
| (41) | 2.50 (100) | 4.40 (100) | 2.53 (100) |
| (42) | 1.87 (87) | 3.65 (100) | 2.05 (100) |
| (43) | 1.83 (80) | 3.71 (97) | 2.09 (92) |
| (44) | 1.91 (90) | 3.88 (100) | 2.14 (100) |
| (45) | 2.28 (100) | 4.06 (100) | 2.31 (100) |
| (46) | 2.06 (100) | 4.03 (100) | 2.19 (100) |
| (47) | 2.35 (100) | 4.57 (100) | 2.32 (100) |
| (48) | 2.59 (100) | 4.69 (100) | 2.54 (100) |
| (49) | 1.60 (70) | 2.81 (90) | 1.97 (74) |
| (50) | 2.48 (100) | 4.36 (100) | 2.48 (100) |
| (51) | 2.52 (100) | 4.50 (100) | 2.50 (100) |
| (52) | 2.25 (100) | 3.82 (100) | 2.26 (100) |
| (53) | 2.31 (100) | 4.15 (100) | 2.33 (100) |
| (54) | 2.27 (100) | 4.04 (100) | 2.19 (100) |
| (55) | 2.49 (100) | 4.67 (100) | 2.46 (100) |
| (56) | 2.74 (100) | 4.59 (100) | 2.58 (100) |
| (57) | 2.55 (100) | 4.13 (100) | 2.50 (100) |
| (58) | 2.69 (100) | 4.40 (100) | 2.42 (100) |
| (59) | 2.13 (100) | 3.95 (100) | 2.24 (100) |
| (60) | 2.06 (100) | 3.91 (100) | 2.23 (100) |
| (61) | 2.48 (100) | 4.33 (100) | 2.49 (100) |
| (62) | 2.11 (100) | 4.07 (100) | 2.17 (100) |
| (63) | 2.26 (100) | 4.26 (100) | 2.20 (100) |
| (64) | 2.62 (100) | 4.52 (100) | 2.57 (100) |
| (65) | 1.54 (70) | 2.80 (92) | 1.93 (72) |
| (66) | 2.82 (100) | 4.82 (100) | 2.80 (100) |
| (67) | 2.55 (100) | 4.49 (100) | 2.56 (100) |
| (68) | 1.49 (65) | 2.77 (88) | 1.89 (70) |
| (69) | 2.76 (100) | 4.74 (100) | 2.65 (100) |
| (70) | 1.94 (94) | 3.80 (100) | 2.08 (100) |
| (71) | 2.60 (100) | 4.33 (100) | 2.54 (100) |
| (72) | 2.29 (100) | 4.09 (100) | 2.31 (100) |
| (73) | 2.31 (100) | 4.25 (100) | 2.34 (100) |
| (74) | 1.97 (92) | 3.97 (100) | 2.10 (100) |
| (75) | 2.24 (100) | 4.12 (100) | 2.27 (100) |
| (76) | 2.30 (100) | 4.20 (100) | 2.36 (100) |
| (77) | 2.06 (100) | 4.09 (100) | 2.18 (100) |
| (78) | 1.83 (80) | 3.02 (97) | 2.06 (84) |
| (79) | 1.53 (72) | 2.61 (90) | 1.88 (78) |
| (80) | 1.94 (94) | 3.38 (100) | 2.09 (100) |
| (81) | 2.58 (100) | 4.63 (100) | 2.50 (100) |
| (82) | 2.46 (100) | 4.37 (100) | 2.47 (100) |
| (83) | 2.39 (100) | 4.29 (100) | 2.40 (100) |
| (84) | 2.31 (100) | 4.12 (100) | 2.32 (100) |
| (85) | 2.05 (100) | 3.81 (100) | 2.16 (100) |
| (86) | 1.94 (90) | 3.87 (100) | 2.13 (100) |
| (87) | 2.25 (100) | 4.04 (100) | 2.29 (100) |
| (88) | 2.28 (100) | 4.15 (100) | 2.24 (100) |
| (89) | 1.50 (72) | 2.63 (94) | 1.87 (78) |
| (90) | 2.31 (100) | 4.29 (100) | 2.35 (100) |
| (91) | 2.19 (100) | 4.06 (100) | 2.20 (100) |
| (92) | 2.47 (100) | 4.52 (100) | 2.51 (100) |
| (93) | 1.83 (84) | 3.50 (197) | 2.04 (90) |
| (94) | 1.91 (87) | 3.89 (100) | 2.05 (94) |
| (95) | 2.06 (100) | 4.01 (100) | 2.20 (100) |
| (96) | 2.03 (92) | 4.05 (100) | 2.17 (100) |
| (97) | 1.97 (90) | 3.92 (100) | 2.08 (100) |
| (98) | 1.62 (70) | 2.83 (94) | 1.99 (72) |
| (99) | 2.53 (100) | 4.38 (100) | 2.46 (100) |
| (100) | 2.57 (100) | 4.40 (100) | 2.51 (100) |
| (101) | 2.30 (100) | 4.27 (100) | 2.32 (100) |
| (102) | 2.28 (100) | 4.16 (100) | 2.30 (100) |
| (103) | 2.31 (100) | 4.24 (100) | 2.29 (100) |
| (104) | 2.49 (100) | 4.45 (100) | 2.43 (100) |
| (105) | 2.55 (100) | 4.39 (100) | 2.48 (100) |
| (106) | 2.42 (100) | 4.06 (100) | 2.37 (100) |
| (107) | 2.59 (100) | 4.38 (100) | 2.43 (100) |
| (108) | 2.37 (100) | 4.19 (100) | 2.34 (100) |

As can be seen from the foregoing test example, the compounds of this invention were found to have a higher knockdown effect than the known allethrin even when they were used in the form of a 0.2% oily preparation containing no synergist at all, and achieved an overall mortality of nearly 100%. The addition of piperonylbutoxide as a synergist rendered the compounds of this invention still more effective in knocking down and killing flies. The mixed oily preparation of each of the compounds of the present invention and phthalthrin was also found to provide a synergistic effect in knocking down and killing flies.

INSECTICIDAL TEST 2: Insecticidal Tests by Fumigation

A mosquito-repellent incense containing 0.5% of each compound according to this invention as an insecticidal component was prepared, and tested for its effect of knocking down adult mosquitoes (*culex pipiens pallens*). The tests were conducted in accordance with the method described in Nagasawa, Katsuta, et al., "Science of Insect Control", 16 (1951), page 176. The effectiveness of each incense was determined relative to that of allethrin. The following results were obtained:

| Compound tested | Probit 4 | Probit 5 | Probit 6 |
|---|---|---|---|
| Control compound | | | |
| Allethrin | 1.00 | 1.00 | 1.00 |
| Compounds of the invention | | | |
| (1) | 1.93 | 1.97 | 2.02 |

-continued

| Compound tested | Probit 4 | Probit 5 | Probit 6 |
|---|---|---|---|
| (4) | 1.81 | 1.85 | 1.88 |
| (7) | 1.78 | 1.81 | 1.84 |
| (11) | 2.04 | 2.07 | 2.10 |
| (16) | 1.75 | 1.78 | 1.81 |
| (19) | 1.79 | 1.82 | 1.84 |
| (23) | 1.83 | 1.87 | 1.90 |
| (26) | 1.44 | 1.48 | 1.52 |
| (30) | 1.89 | 1.93 | 1.98 |
| (34) | 1.56 | 1.59 | 1.63 |
| (37) | 1.67 | 1.70 | 1.74 |
| (41) | 1.75 | 1.79 | 1.82 |
| (46) | 1.63 | 1.66 | 1.70 |
| (49) | 1.39 | 1.42 | 1.46 |
| (51) | 1.98 | 2.01 | 2.05 |
| (54) | 1.72 | 1.76 | 1.79 |
| (56) | 1.84 | 1.87 | 1.91 |
| (59) | 1.72 | 1.76 | 1.79 |
| (63) | 1.64 | 1.67 | 1.70 |
| (66) | 2.25 | 2.30 | 2.34 |
| (69) | 2.01 | 2.03 | 2.08 |
| (73) | 1.81 | 1.84 | 1.88 |
| (79) | 1.39 | 1.43 | 1.46 |
| (83) | 1.88 | 1.91 | 1.95 |
| (85) | 1.63 | 1.67 | 1.70 |
| (88) | 1.97 | 2.01 | 2.05 |
| (92) | 1.72 | 1.76 | 1.79 |
| (95) | 1.69 | 1.73 | 1.75 |
| (98) | 1.44 | 1.48 | 1.51 |
| (101) | 1.50 | 1.55 | 1.58 |
| (103) | 1.66 | 1.69 | 1.72 |
| (107) | 1.58 | 1.63 | 1.67 |

In the table above, Probits 4, 5 and 6 mean the test insect knockdown rate of 16%, 50% and 84%, respectively. The figures shown in the column of each probit indicate the relative effectiveness of each compound tested, which was calculated from the time required for the prescribed knockdown rate. The results shown therein indicate that the compounds of this invention are more effective than allethrin, and useful as the active ingredient of a fumigant, too.

INSECTICIDAL TEST 3: Insecticidal Tests by Topical Application

The tests were conducted on phenpropanate(3'-phenoxy-2'-cyanobenzyl 2,2,3,3-tetramethylcyclopropanecarboxylate), various compounds according to this invention, and an acetone solution having a predetermined concentration, and containing phenpropanate or each compound according to this invention as an active ingredient, and twice as large a quantity of N-octyl-1-isopropyl-4-methylbicyclo [2,2,2]octo-5-ene-2,2-dicarboxyimide as the active ingredient. Each insecticidal solution thus prepared was applied by a microsyringe to breast and the back of an adult housefly. The insecticidal effect of each compound was determined relative to phenpropanate based on the mortality of the houseflies after 24 hours. The synergistic effect with synepirin 500 was also examined. The following results were obtained:

| Compound tested | Relative insecticidal activity | Relative insecticidal activity with synergist added | Increased by (times) |
|---|---|---|---|
| Phenpropanate | 1.00 | 2.15 | 2.2 |
| Compounds of the invention | | | |
| (1) | 3.24 | 11.02 | 3.4 |
| (2) | 3.50 | 10.15 | 2.9 |
| (3) | 2.86 | 9.15 | 3.2 |
| (4) | 2.77 | 9.70 | 3.5 |
| (5) | 3.31 | 9.27 | 2.8 |
| (7) | 3.03 | 8.18 | 2.7 |
| (15) | 4.12 | 11.54 | 2.8 |
| (28) | 2.95 | 8.85 | 3.0 |
| (29) | 3.06 | 9.49 | 3.1 |
| (31) | 2.82 | 9.31 | 3.3 |
| (57) | 3.16 | 8.85 | 2.8 |
| (64) | 2.94 | 9.41 | 3.2 |
| (77) | 2.86 | 9.44 | 3.3 |
| (81) | 3.05 | 8.85 | 2.9 |

| Compound Tested | Relative Insecticidal Activity | Relative Insecticidal Activity with Synergist Added | Increased by (times) |
|---|---|---|---|
| 94 | 3.23 | 9.69 | 3.0 |
| 105 | 3.61 | 9.75 | 2.7 |

As is obvious from the table, it is possible to increase the insecidal activity of the compounds according to this invention by at least about three times if N-octyl-1-isopropyl-4-methylbicyclo [2,2,2]octo-5-ene-2,2-dicarboxyimide is added. This means that it is sufficient to employ a smaller quantity of compound according to this invention to obtain a higher insecticidal effect.

INSECTICIDAL TEST 4

1/1000 water-diluted solutions of emulsifiable concentrate containing the compounds 3, 6, 10, 18, 23, 31, 38, 40, 48, 53, 58, 61, 65, 72, 76, 84, 89, 91 and 106, respectively, of this invention prepared in accordance with the procedures to be set forth later in Example 3 for Insecticide Preparation was sprinkled at a rate of 100 liters per 'tan' (0.245 acre) in a field of Japanese radishes of five or six leaf stages on which a lot of green peach aphides (Myzus Persicae Sulzer) was infested. After two days, the density of the aphides in each lot of the field was examined with respect to the parasites, and found to be 10% or less of that which had prevailed prior to the application of the insecticide.

INSECTICIDAL TEST 5

Cabbage leaves were immersed for about five seconds into 1/2000 diluted solutions of emulsifiable concentrates containing the compounds 1, 6, 12, 16, 21, 29, 33, 38, 42, 46, 52, 56, 61, 67, 70, 75, 82, 86, 89, 93, 96 and 101, respectively, of this invention prepared in accordance with the procedures to be set forth later in Example 3 for Insecticide Preparation. After the solutions had dried up, the leaves were placed in a glass dish, and ten sound larvae of cabbage armyworm were settled free on the leaves. The insects were set free twice, i.e., on the day when the leaves had been dipped in the insecticidal solution, and five days thereafter. The mortality of the insects was examined after 24 hours. The results were shown in the following table.

| Compound tested | At the day dipped | 5 days later |
|---|---|---|
| Salithion emulsion | 40 (%) | 5 (%) |

| Compound tested | At the day dipped | 5 days later |
|---|---|---|
| Emulsions of the compounds of the invention | | |
| (1) | 100 | 95 |
| (6) | 100 | 100 |
| (12) | 90 | 65 |
| (16) | 90 | 60 |
| (21) | 95 | 80 |
| (29) | 100 | 100 |
| (33) | 95 | 85 |
| (38) | 90 | 65 |
| (42) | 95 | 75 |
| (46) | 100 | 70 |
| (52) | 100 | 95 |
| (56) | 100 | 95 |
| (61) | 100 | 100 |
| (67) | 95 | 60 |
| (70) | 90 | 65 |
| (75) | 95 | 80 |
| (82) | 100 | 100 |
| (86) | 90 | 85 |
| (89) | 90 | 60 |
| (93) | 95 | 75 |
| (96) | 95 | 70 |
| (101) | 100 | 90 |

The test results indicate the higher insecticidal activity and persistency of the compounds according to this invention, as compared with the salithion emulsion employed as the control.

INSECTICIDAL TEST 6

About 200 aphides (*Aphis craccivora* Koch) were put free on each broad bean plant (*Vicia faba* L) in a pot one day prior to the application of an insecticide. 1/4000 diluted solutions of wettable powders containing the compounds 5, 13, 17, 24, 28, 32, 36, 44, 47, 55, 60, 68, 71, 77, 81, 94, 97, 104 and 108, respectively, of this invention prepared in accordance with the procedures to be set forth later in Example 8 for Insecticide Preparation were sprayed by compressed air onto the leaves with the harmful insects at a rate of 10 ml per pot. After two days, the degree of damage was examined, and none of them was found to suffer from an increased damage.

INSECTICIDAL TEST 7

Each of powders of the compounds 1, 7, 14, 20, 25, 35, 39, 42, 49, 54, 56, 62, 74, 80, 86, 90, 93, 98 and 103, respectively, of this invention prepared in accordance with the procedures to be set forth later in Example 7 of Insecticide Preparation was spread uniformly at a rate of 2 g/m² in the bottom of a tall glass dish having a diameter of 14 cm. Butter was applied onto the inner wall surface of the dish, except for the portion of a height of about 1 cm from its bottom. A group of 10 imagines of B lattella germanicas were placed free in each dish, and after half an hour of exposure to the powder, they were transferred into a separate container for observation. After three days, all of the powders according to this invention were found capable of killing at least 80% of the germanicas.

ACARICIDAL TEST

Ten adult female carmine spider mites were put free on each of the four leaves of a kidney bean plant in a pot five days after seeding. The pot was kept in a room having a constant temperature of 27° C. After 6 days, 100 ppm water diluted solution of emulsifiable concentrates of the compounds 4, 6, 11, 15, 21, 26, 32, 34, 43, 50, 59, 61, 66, 69, 75, 79, 87, 99 and 105, respectively, of this invention prepared in accordance with the procedures to be set forth later in Example 3 for Insecticide Preparation were sprinkled to the pots on a twin table at the rate of 10 ml/pot. After 10 days, the plants were examined and only 10 or fewer ticks were found on each plant.

The invention will now be described with reference to examples of insecticide preparation. These insecticides may be prepared without any particular limitation by any method well known to the ordinarily skilled in the art of agricultural chemicals.

INSECTICIDE PREPARATION

EXAMPLE 1

Kerosine was added to 0.2 part of each of the compounds 1, 5, 9, 13, 34, 56, 68 and 85 of this invention to make 100 parts of 0.2% of oily preparation.

EXAMPLE 2

Kerosine was added to 0.2 part of each of compounds 4, 10, 17, 38, 59 and 96 of this invention and 0.8 part of piperonyl butoxide to make 100 parts of oily preparation.

EXAMPLE 3

10 parts of Solpol SM-200 (Registered Trademark of Toho Chemical) and 70 parts of xylole were added to 20 parts of each of the compounds 6, 16, 42, 61, 75 and 101 of this invention and were mixed together for dissolution under stirring to form a 20% emulsifiable concentrate.

EXAMPLE 4

0.4 part of each of the compounds 12, 45, 67 and 89 of this invention, 0.1 part of resmethrin and 1.5 parts of octachlorodipropylether were dissolved in 28 parts of refined kerosine. The solution was packed into an aerosol container and after a valve arrangement had been attached to the container, 70 parts of a jetting agent (liquefied petroleum gas) were filled under pressure into the container through its valve arrangement to prepare an aerosol.

EXAMPLE 5

0.5 g of each of the compounds 7, 19, 63, 72 and 103 of this invention and 0.5 g of BHT were mixed uniformly with 99.0 g of a substrate for a mosquito-repellent incense, such as pyrethrum, wood flour starch and the like. The mixture was formed into a mosquito-repellent incense by a known method.

EXAMPLE 6

0.4 g of each of the compounds 11, 54, 79 and 98 of this invention and 1.0 g of MGK-5026 were mixed uniformly with 98.6 g of a substrate for a mosquito-repellent incense. The mixture was formed into a mosquito-repellent incense by a known method.

EXAMPLE 7

Three parts of each of the compounds 14, 35 and 86 of this invention and 97 parts of clay were crushed well and mixed together to yield a 3% powder.

EXAMPLE 8

A wettable powder was obtained by crushing and mixing 40 parts of each of the compounds 24, 47, 77 and 97 of this invention, 35 parts of diatomaceous earth, 20 parts of clay, 3 parts of a laurylsulfonate and 2 parts of carboxymethyl cellulose.

We claim:

1. A cyclopropanecarboxylic acid ester derivative of the general formula I:

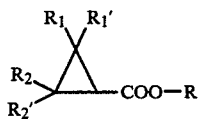

in which $R_1$ stands for a methyl group, a halogen atom or a halomethyl group, $R_1'$ stands for a halomethyl or haloethyl group, $R_2$ and $R_2'$ are the same or different, each standing for a methyl group, a halogen atom or a halomethyl group, and R stands for a group of the formula II, III, IV, V or VI:

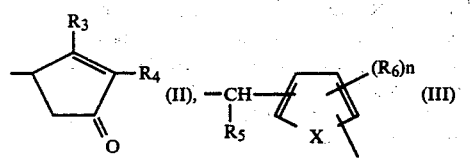

in which $R_3$ stands for a hydrogen atom or a methyl group, $R_4$ stands for an allyl, propargyl, benzyl or 2,4-pentadienyl group, X stands for an oxygen or sulfur atom or a —CH=CH— group, $R_5$ stands for a hydrogen atom, or a cyano, ethynyl, propynyl or trifluoromethyl group, $R_6$ stands for a hydrogen or halogen atom, or a methyl or trifluoromethyl group, n is an integer of 1 to 4, $R_7$ stands for a halogen atom, a lower alkyl, lower haloalkoxy or lower haloalkoxymethyl group, an allyl, propargyl, benzyl, benzoyl or phenoxy group, a phenoxy group in which one hydrogen atom in the benzene ring has been replaced by a halogen atom, or a methyl or lower alkoxy group, or a dichlorovinyloxy group, $R_5$ and $R_6$ may have their ends bonded to each other to form an ethylene or methyleneoxy chain, and $R_6$ and $R_7$ may have their ends bonded to each other to form a trimethylene or tetramethylene chain, $R_8$ stands for a hydrogen atom, or an ethynyl group, $R_9$ and $R_9'$ each stand for a hydrogen or halogen atom, or a methyl group, $R_{10}$ stands for a phenyl or benzyl group, or an alkyl, alkenyl or alkynyl group having 2 to 4 carbon atoms, $R_{11}$ stands for a tetrahydrophthalimide or dialkylmaleimide group, and $R_{12}$ stands for a phenyl or phenoxy group; and an optical or geometrical isomer thereof.

2. A compound as set forth in claim 1, said compound being represented by the general formula VII:

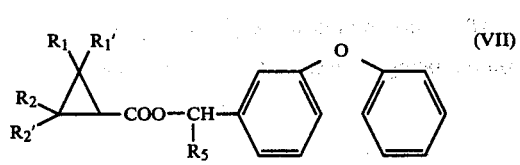

in which $R_1$ stands for a methyl group, a halogen atom or a halomethyl group, $R_1'$ stands for a halomethyl or haloethyl group, $R_2$ and $R_2'$ are the same or different, each standing for a methyl or halomethyl group, or a halogen atom, and $R_5$ stands for a hydrogen atom, or a cyano, ethynyl, propynyl or trifluoromethyl group.

3. A compound as set forth in claim 2, wherein in said formula VII, $R_1$ and $R_2$ each stand for a trifluoromethyl group, and $R_5$ stands for a cyano group.

4. A compound as set forth in claim 3, said compound being represented by the formula:

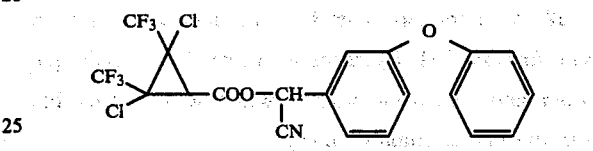

5. A compound as set forth in claim 3, said compound being represented by the formula:

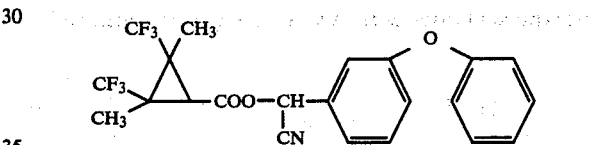

6. A compound as set forth in claim 3, said compound being represented by the formula:

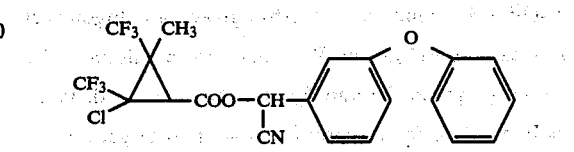

7. A compound as set forth in claim 2, wherein in said formula VII, $R_1$ stands for a trifluoromethyl group, $R_2$ and $R_2'$ each stand for a methyl group, and $R_5$ stands for a cyano group.

8. A compound as set forth in claim 7, said compound being represented by the formula:

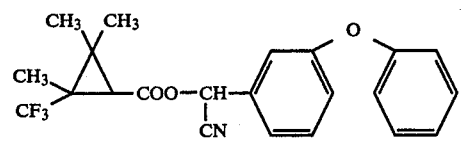

9. A compound as set forth in claim 7, said compound being represented by the formula:

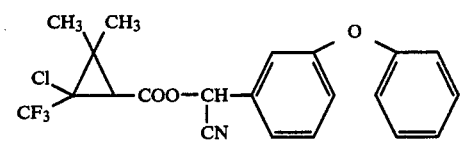

10. A compound as set forth in claim 7, said compound being represented by the formula:

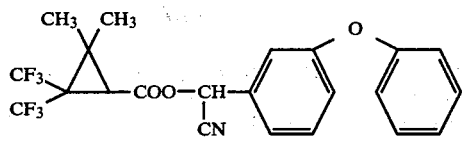

11. A compound as set forth in claim 1, wherein the substituents $R_1$ and $R_1'$, and $R_2$ and $R_2'$ in said formula I have different combinations, and the carbon in the α-position relative to the carboxyl group in the cyclopropane ring has the absolute configuration (R).

12. A compound as set forth in claim 2, wherein in said formula VII, $R_5$ stands for other than a hydrogen atom, and the carbon atom to which $R_5$ is bonded has the absolute configuration (S).

13. An insecticidal and acaricidal composition comprising an insecticidal quantity of a cyclopropanecarboxylic acid ester derivative of the general formula I:

in which $R_1$ stands for a methyl group, a halogen atom or a halomethyl group, $R_1'$ stands for a halomethyl or haloethyl group, $R_2$ and $R_2'$ are the same or different, each standing for a methyl or halomethyl group, or a halogen atom, and R stands for a group of the formula II, III, IV, V or VI:

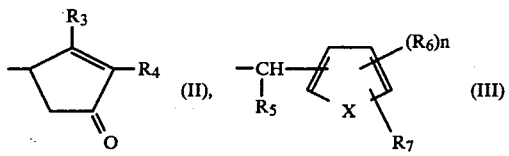

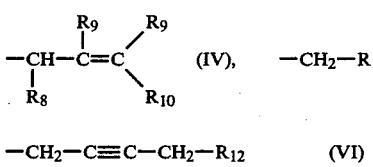

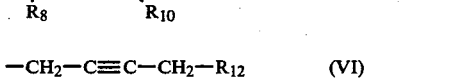

in which $R_3$ stands for a hydrogen atom or a methyl group, $R_4$ stands for an allyl, propargyl, benzyl or 2,4-pentadienyl group, X stands for an oxygen or sulfur atom, or a —CH=CH— group, $R_5$ stands for a hydrogen atom, or a cyano, ethynyl, propynyl or trifluoromethyl group, $R_6$ stands for a hydrogen or halogen atom, or a methyl or trifluoromethyl group, n is an integer of 1 to 4, $R_7$ stands for a halogen atom, a lower alkyl, lower haloalkoxy or lower haloalkoxymethyl group, an allyl, propargyl, benzyl, benzoyl or phenoxy group, a phenoxy group in which one hydrogen atom in the benzene ring has been replaced by a halogen atom, or a methyl or lower alkoxy group, or a dichlorovinyloxy group, $R_5$ and $R_6$ may have their ends bonded to each other to form an ethylene or methyleneoxy chain, and $R_6$ and $R_7$ may have their ends bonded to each other to form a trimethylene or tetramethylene chain, $R_8$ stands for a hydrogen atom or an ethynyl group, $R_9$ stands for a hydrogen or halogen atom, or a methyl group, $R_{10}$ stands for a phenyl or benzyl group, or an alkyl, alkenyl or alkynyl group having 2 to 4 carbon atoms, $R_{11}$ stands for a tetrahydrophthalimide or dialkylmaleimide group, and $R_{12}$ stands for a phenyl or phenoxy group; and an inert filler.

14. An insecticidal and acaricidal composition as set forth in claim 13, further comprising as an assistant one or two pyrethroid synergists selected from the group consisting of piperonyl butoxide, octachlorodipropylether, N-octylbicycloheptanedicarboxyimide, and N-octyl-1-isopropyl-4-methylbicyclo-[2,2,2]-octo-5-ene-2,2-dicarboxyimide in a necessary amount.

* * * * *